United States Patent
Weissmann et al.

(10) Patent No.: US 8,771,953 B2
(45) Date of Patent: Jul. 8, 2014

(54) EVALUATION OF THE POTENTIAL RISK OF DRUG INDUCED MOOD DISTURBANCE AND SUICIDE: USE OF A DEDICATED PLATFORM

(75) Inventors: Dinah Weissmann, Paris (FR); Jean-Francois Pujol, Paris (FR); Laurent Vincent, Bondoufle (FR); Laurent Cavarec, Vincennes (FR)

(73) Assignee: Biocortech, Paris (FR)

( * ) Notice: Subject to any disclaimer, the term of this patent is extended or adjusted under 35 U.S.C. 154(b) by 138 days.

(21) Appl. No.: 13/140,325

(22) PCT Filed: Dec. 17, 2009

(86) PCT No.: PCT/EP2009/067464
§ 371 (c)(1),
(2), (4) Date: Jun. 16, 2011

(87) PCT Pub. No.: WO2010/070074
PCT Pub. Date: Jun. 24, 2010

(65) Prior Publication Data
US 2012/0129177 A1      May 24, 2012

(30) Foreign Application Priority Data

Dec. 17, 2008   (EP) .................................. 08305963

(51) Int. Cl.
*C12Q 1/68* (2006.01)
(52) U.S. Cl.
USPC ........................................................ 435/6.12
(58) Field of Classification Search
None
See application file for complete search history.

(56) References Cited

U.S. PATENT DOCUMENTS

| | | | |
|---|---|---|---|
| 2005/0208496 A1* | 9/2005 | Ohtani et al. | 435/6 |
| 2007/0083334 A1* | 4/2007 | Mintz et al. | 702/19 |
| 2008/0075662 A1* | 3/2008 | Madjar et al. | 424/9.2 |
| 2010/0184058 A1* | 7/2010 | Weissmann | 435/6 |

FOREIGN PATENT DOCUMENTS

| WO | WO 2006/134128 A2 | 12/2006 |
|---|---|---|
| WO | WO 2008/152146 A1 | 12/2008 |

OTHER PUBLICATIONS

Yang et al. (Altered RNA editing of serotonin 5-HT2C receptor induced by interferon: implications for depression associated with cytokine therapy, Molecular Brain Research 124 (2004) 70-78).*
Flomen et al. (Evidence that RNA editing modulates splice site selection in the 5-HT2C receptor gene, Nucleic Acids Research, 2004, vol. 32, No. 7, pp. 2113-2122).*
Poyau et al. (Identification and relative quantification of adenosine to inosine editing in serotonin 2c receptor mRNA by CE, Electrophoresis 2007, 28, 2843-2852).*
Chanrion et al. (Inverse Agonist and Neutral Antagonist Actions of Antidepressants at Recombinant and Native 5-Hydroxytryptamine2C Receptors: Differential Modulation of Cell Surface Expression and Signal Transduction, Mol Pharmacol 73:748-757, 2008).*
NCBI Accession #: AH013751.*
NCBI Accession #: HSU73197.*
Jayan et al., "Inhibition of Hepatitis Delta Virus RNA Editing by Short Inhibitory RNA-Mediated Knockdown of ADAR1 but Not ADAR2 Expression," Journal of Virology, vol. 76, No. 23, pp. 12399-12404, Dec. 2002.
Werry et al., "RNA editing of the serotonin $5HT_{2c}$ receptor and its effects on cell signaling, pharmacology and brain function," Pharmacology & Therapeutics, vol. 119, pp. 7-23, 2008.
Yang et al., "Altered RNA editing of serotonin $5\text{-}HT_{2c}$ receptor induced by interferon: implications for depression associated with cytokine therapy," Molecular Brain Research, vol. 124, pp. 70-78, 2004.
International Search Report issued for application No. PCT/EP2009/067464 on Aug. 13, 2010.
Cavarec, L., et al., "In Vitro Screening for Drug-Induced Depression and/or Suicidal Adverse Effects: A New Toxicogenomic Assay Based on CE-SSCP Analysis of HTR2C mRNA Editing in SH-SY5Y Cells," Neurotoxicity Research, Published online 2012, pp. 1-16.

* cited by examiner

*Primary Examiner* — Christopher M Babic
*Assistant Examiner* — Aaron Priest
(74) *Attorney, Agent, or Firm* — Foley & Lardner LLP

(57) ABSTRACT

The present invention relates to in vitro methods for the determination of the potential toxicity of test compounds. The invention also comprises in vitro methods for the selection of therapeutical compounds useful for the treatment of pathology related to an alteration of the mechanism of the mRNA editing of ADAR dependent A to I mRNA editing of the serotonin 2C receptor (5HTR2C). Finally, the present invention is directed to the kits and tools for the implementation of these methods. The invention is of special utility in the pharmaceutical industry for analysis of the toxicity profile or the screening of compounds involved in drug development and/or in pharmaceutical compositions.

29 Claims, 6 Drawing Sheets

FIGURE 4

Figure 1A:
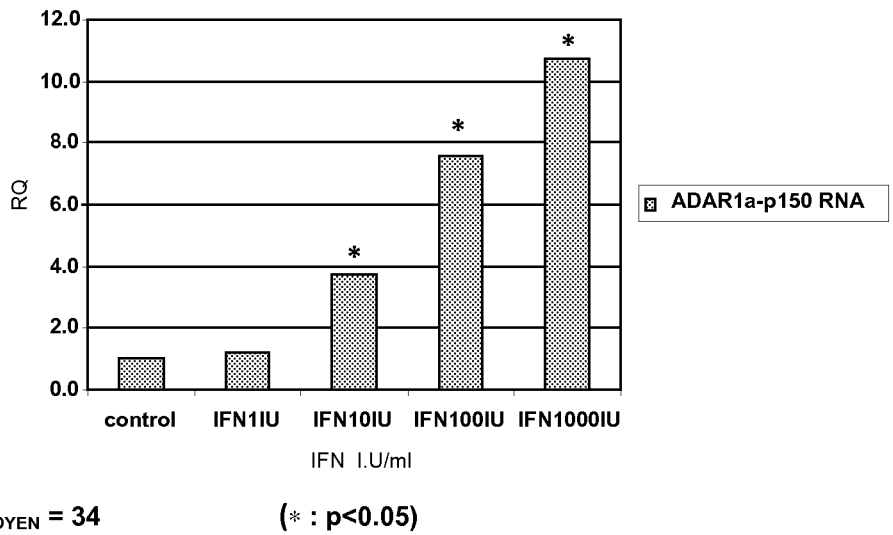

EVALUATION OF THE POTENTIAL RISK OF DRUG INDUCED MOOD DISTURBANCE AND SUICIDE: USE OF A DEDICATED PLATFORM

The present invention relates to in vitro methods for the determination of the potential toxicity of test compounds. The invention also comprises in vitro methods for the selection of therapeutical compounds useful for the treatment of pathology related to an alteration of the mechanism of the mRNA editing of ADAR dependent A to I mRNA editing of the serotonin 2C receptor (5HTR2C). Finally, the present invention is directed to the kits and tools for the implementation of these methods. The invention is of special utility in the pharmaceutical industry for analysis of the toxicity profile or the screening of compounds involved in drug development and/ or in pharmaceutical compositions.

Toxicity is the major reason for abandoning candidate therapeutic molecules during preclinical and clinical development. To our knowledge, at the present time there is a need to provide with tests by which to rapidly determine the toxicity profile of a compound in man. In general, such tests are long and costly and are only partially satisfactory. For example, animal toxicity is far from being a reflection of human toxicity. Furthermore, the small number of patients enrolled in clinical trials does not systematically allow identification of toxicities associated with a small, specific population. The development, perfection and use of such tests should make it possible to identify and remove toxic compounds from the development process as far upstream as possible. In this manner new drugs could be marketed sooner and at a lesser cost to drug companies and, in turn, to health care organizations and consumers. In addition, such tests might also make it possible to detect some toxicities which currently come to light only during the post-marketing period.

Genetic association studies, knockout mice and postmortem analysis have suggested the implication of the serotonin 2C receptor (HTR2C) in neuropsychiatric disorders. Firstly, a functional allelic polymorphism (Cys23Ser) of HTR2C is associated with depression and bipolar disorder (Lerer et al., 2001, Mol. Psychiatry, 6: 579-585). Secondly, mice lacking the 5-HT2C serotonin receptor exhibit spontaneous convulsions, cognitive impairment and abdormal control of feeding behavior (Tecott et al., 1995, Nature, 374:542-546). These animals are also hyperresponsive to repeated stress (Chougreen et al., 2003, Physiol. Behav., 79:217-226). Thirdly, in postmortem brains of patients affected by bipolar disorder or schizophrenia, the RNA expression of the 5-HT2C serotonin receptor is down-regulated (Iwamoto et al., 2004, Mol. Psychiatry, 9: 406-416; Castensson et al., 2003, Biol. Psychiatry, 54: 1212-1221) RNA editing of HTR2C is also thought to be involved in the pathophysiology of mental disorders and the action of antidepressants (Seeburg, 2002, Neuron, 35: 17-20). Five adenosine residues (named A, B, C, D and E or C') are edited in a region coding for the second intracellular loop of the 5-HT2C serotonin receptor and can lead to amino-acid substitutions at three different positions of the receptor sequence. The combinational substitution of these amino residues generates up to 24 different HTR2C protein isoforms with different G-coupling efficiencies (Price et al., 2001, J. Biol. Chem., 276: 44663-44668). In mice, when compared with C57BL/6 and 129sv inbred strains, the BALB/c strain exhibits a different basal forebrain neocortical 5-HT2C pre-mRNA editing pattern that may underlie their difference in stress reactivity. Moreover, the BALB/c mice exhibit stress-induced changes in 5-HT2C pre-mRNA editing resembling those detected in brains of depressed suicide victims (Englander et al., 2005, J. Neurosci., 25: 648-651). Actually, in postmortem brains, altered RNA editing of HTR2C has been reported in patients with schizophrenia, depression and those who committed suicide (Niswender et al., 2001, Neuropsychopharmacology, 24: 478-491; Sodhi et al., 2001, Mol. Psychiatry, 6:373-379; Gurevich et al., 2002, Neuron, 34: 349-356; Dracheva S. et al. 2008, Molecular Psychiatry 13, 1011-10). Additionally interferon a is used in hepatitis C treatment but symptoms of depression often appear' as a side effect of this molecule in patients and Yang et al. have demonstrated that this molecule strongly alters the editing of 5HT2C receptor (see ref. in Tohda et al., 2006, J. Pharmacol Sci, 100, 427-432).

Previous studies have shown that the 5-HT2C serotonin receptor is mainly expressed in the brain, particularly in choroid plexus, prefrontal cortex, limbic areas, basal ganglia and hypothalamus (Tohda et al., 1996, Neurosci. Res., 24: 189-193; Julius et al., 1988, 241: 558-564; Pasqualetti et al., 1999, Neuroscience, 92: 601-611). This brain specific pattern of expression restricts investigations of potential links existing between HTR2C RNA editing and psychiatric condition to postmortem studies.

New method were recently developed which allows to quantify from total tissue RNA the complete editing profile of 5-HT2CR by one single assay (Poyau et al., 2007, Electrophoresis, 28, 2843-52). It determines the percentage of each edited and non edited isoforms in the fraction of specific mRNA contained in the tissue sample. It is well adapted to the evaluation of editing variations in specific brain regions in Mouse, Rat and Man. This Kind of technology has been successful to analyse the editing profile in primary cultured neural cells (Chanrion B., et al., Molecular Pharmacol, 2008, 73, 748-57).

The inventors main interest of this evaluation is to allows to extract from the profile an index of the activity of the editing isoenzymes the ADARs 1a, 1b, ADAR2 since ADAR1 isoenzymes edit the sites A, B and also C and E and the ADAR2 can edit the sites D and C and E. It is thus actually admitted that an isoform in which the sites A and/or B are edited have been transformed by the ADARs I isoenzymes, acting alone if the D site is not edited (the edited isoforms: A, AB, ABC, ABCE, ABE, AC, ACE, AE, B, BC, BCE, BE), or acting together with ADAR2 if the isoforms presents also the edited D site (the edited isoforms: ABCD, ABCDE, ABD, ABDE, ACD, ACDE, AD, ADE, BCD, BCDE, BD, BDE, C, CE, E).

The iso forms in which the sites A and/or B are not edited and the D site is edited are considered as the result of the action of ADAR2 alone.

Together to this analysis of the complete editing profile of the 5-HT2C R, the inventors have demonstrated that an evaluation of the expression of the ADARs isoenzymes as a complementary approach is particularly well adapted to the evaluation of the general editing context of dysregulation of the editing machinery. It includes the quantitative and qualitative analysis of ADARs isoenzymes expression (mRNA, i.e. by quantitative RT-PCR, and/or the corresponding encoded protein, i.e. by the western blotting).

Considering the special warning of the Food and Drug Administration (FD) about suicide risk to epilepsy drug, to antidepressants and antipsychotics. For example, recently the weight-loss drug Acomplia™ (rimonabant) was found as triggering suicidal behavior and other psychological side effects in some patients, these known neuropsychiatric side effects rendering difficult for the FDA and the European Medicines Agency to see a positive risk-benefit ratio for this new drug and finally recommended pulling it from the market because of its side effects.

As mentioned above, there is a need to provide with tests which can rapidly determine the toxicity or potential side-effects profile of a drug in man, particularly before the post-marketing period.

It is the reason why the inventors have decided to develop a dedicated platform which could be proposed to evaluated, for example at a pre-clinical stage, the potential effect of new therapeutic molecules on the editing regulation since editing has been already found altered in patients suffering from depression, psychosis or having committed suicide.

The inventors have demonstrated that:

using particular mammal cells lines, particularly human cells lines, which expressed the editing enzymes ADAR1a, ADAR1b and ADAR2 and the 5-HT2C receptor; and comparing between control cells and treated cells with the compound to be tested a) the activity of these editing enzymes (obtained by analysis of the editing profile giving the mean proportion of each identified iso form of the 5-HT2CR mRNA measured in the cellular RNA extract); and/or b) the quantitative expression of these editing enzymes ADAR1a, ADAR1b and ADAR2 (i.e. by Q-PCR or by western blotting), it is possible to predict the eventual risk of these compounds to produce altered mood by a chronic alteration of the 5-HT transmission.

The present invention now describes rapid, effective methods by which to determine the potential toxicity of efficiency of test compounds, as well as the tools and kits for the implementation of such methods.

Thus, the present invention is directed to an in vitro method for the determination or for the prediction of the potential toxicity or side-effects of a test compound which can result after its administration in a patient, comprising the following steps of:

a) obtaining a biological sample containing mammal cells wherein said mammal cells express the editing enzymes ADAR1a, ADAR1b and ADAR2 and the serotonin 2C receptor (5HTR2C);

b) contacting said mammals cells with the compound to be tested;

c) determining in the same cellular extract:

the editing profile giving the mean proportion of each identified isoform of the 5-HT2CR mRNA measured in the cellular RNA extract, and/or the quantitative expression of said editing enzymes ADAR1a, ADAR1b and ADAR2;

d) comparing the results obtained in step c) between said treated cells with the compound to be tested and non treated control cells or cells contacted with a control compound.

In the context of the invention, the term "toxicity" refers to any adverse and/or side effect of a compound on the metabolism of a cell or a tissue and more generally any alteration in metabolism that can result in a harmful effect of the compound on the patient, particularly in the context of the present invention the potential risk of drug induced mood disturbance and suicide.

The term "test compound" refers in general to a compound to which a test subject is exposed. Typical test compounds will be small organic molecules, typically drugs and/or prospective pharmaceutical lead compounds, but can include proteins, peptides, polynucleotides, heterologous genes (in expression systems), plasmids, polynucleotide analogs, peptide analogs, lipids, carbohydrates, viruses, phages, parasites, and the like.

The term "control compound" refers to a compound that is not known to share any biological activity with a test compound, which is used in the practice of the invention to contrast "active" (test) and "inactive" (control) compounds during the derivation of Group Signatures and Drug Signatures. Typical control compounds include, without limitation, drugs used to treat disorders distinct from the test compound indications, vehicles, inactivated versions of the test agent, known inert compounds, and the like.

In a second aspect, the present invention is also directed to an in vitro method for the selection of a therapeutical compounds useful for the treatment of pathology related to an alteration of the mechanism of the mRNA editing of ADAR dependent A to I mRNA editing of the 5-HTR2C comprising the following steps of:

a) obtaining a biological sample containing mammal cells wherein said mammal cells expressing the editing enzymes ADAR1a, ADAR1b and ADAR2 and the 5-HT2C receptor;

b) contacting said mammals cells with the compound to be tested;

c) determining in the same cellular extract:

the editing profile giving the mean proportion of each identified isoform of the 5-HT2CR mRNA measured in the cellular RNA extract, and/or the quantitative expression of said editing enzymes ADAR1a, ADAR1b and ADAR2;

d) comparing the results obtained in step c) between said treated cells with the compound to be tested and non treated control cells or cells contacted with a control compound; and e) selecting the tested compound, whether this tested compound exhibits the alteration or the non alteration of the HT2CR editing profile and/or of the editing enzymes ADAR1a, ADAR1b and ADAR2 activities which is desired to obtain.

In a preferred embodiment, the present invention is directed to an in vitro method for the determination or for the prediction of the potential toxicity or side-effects of a test compound or for the selection of a therapeutical compounds, wherein step c) comprises determining in the same cellular extract:

the editing profile giving the mean proportion of each identified isoform of the 5-HT2CR mRNA measured in the cellular RNA extract, and, optionally the quantitative expression of said editing enzymes ADAR1a, ADAR1b and ADAR2.

In an even more preferred embodiment, the present invention is directed to an in vitro method for the determination or for the prediction of the potential toxicity or side-effects of a test compound or for the selection of a therapeutical compounds, wherein step c) comprises determining in the same cellular extract:

the editing profile giving the mean proportion of each identified isoform of the 5-HT2CR mRNA measured in the cellular RNA extract, and the quantitative expression of said editing enzymes ADAR1a, ADAR1b and ADAR2.

In a preferred embodiment, in step a) of the methods of the present invention, said mammal cells are capable of expressing of a significant number of edited iso forms of 5HT2CR mRNA demonstrating that these ADAR1a, ADAR1b and ADAR2 enzymes are active to control the production of several edited iso forms of the receptor in these cells.

More preferably, these mammal cells are able to present at least the sites A, B and also C and E edited, also more preferred are mammals cells which can present at least 1, preferably 2, 3, 4, 5, 6, 7, 6, 9, 10, 11 and 12, edited ADAR 1 isoforms selected from the group consisting of A, AB, ABC, ABCE, ABE, AC, ACE, AE, B, BC, BCE, BE edited isoforms, together with at least 1, preferably 2, 3, 4, 5, 6, 7, 6, 9, 10, 11, 12, 13 14 and 15 isoforms presenting also the edited D site selecting from the group of the edited isoforms ABCD, ABCDE, ABD, ABDE, ACD, ACDE, AD, ADE, BCD, BCDE, BD, BDE, C, CE and E.

In a preferred embodiment of the methods of the present invention in step a), said mammal cells are cells lines, particularly from human, mouse or rat.

In a more preferred embodiment of the methods of the present invention in step a), said mammal cells are mammal cells lines, particularly from human, mouse or rat, which exhibit a regular and constitutive expression of the 5HT2CR, ADAR1 and ADAR2 enzymes, preferably ADAR1a, ADAR1b and ADAR2 enzymes.

The characteristic "exhibit a regular and constitutive expression of the 5HT2CR, ADAR1 and ADAR2 enzymes, preferably ADAR1a, ADAR1b and ADAR2 enzymes" is very important in the sense where the expression of the content of the 5HT2CR, ADAR1 and ADAR2 enzymes are to be constant (regular) when the cells are cultured and untraited (control cells) in order to have reliable comparative data with traited cells (robustness and reliability of the assay).

For example, the inventors have surprisingly demonstrated (see Example 5 table 5 that the HTB-14 cells (glioma cells line) do not express enough regular and constitutive 5HT2CR and cannot be used as mammal cells line in the method of the present invention.

The expression of the editing enzymes ADARs alone is not sufficient to predict the potential toxicity or side effects of a test compound or for selecting a therapeutical compound according to the present invention, or to find new reference compound (as interferon alpha) for comparing the effect of tested compound on the alteration of the 5HT2CR edition and to predict the potential toxicity or side-effects in view of the known alteration and toxicity/side-effects of these reference compounds (panel of reference compounds wherein their effects on the alteration of the 5HT2CR edition have been studied on the mammal cell lines used in the method of the present invention (such as neuroblastoma cell line (i.e. SH-SY5Y) and wherein the potential toxicity or side-effects are known) in view of the known alteration and toxicity/side-effects of these reference compounds.

Indeed, the quantitative expression of ADARs is not sufficient to predict their combined effect on the 5HT2C edition. The ADARs quantification assay is not an activity assay and the inventors have demonstrated that only the determination of the distribution of all the 5HT2C isoforms is significant if the real alteration of the 5HT2C edition. It is the reason why it is preferable to determine the distribution of all the 5HT2C isoforms in correlation with the editing enzyme action.

In a yet more preferred embodiment of the methods of the present invention in step a), said mammal cells are mammal cells lines, particularly from human, mouse or rat, having the following characteristics:
1) having a regular and constitutive expression of the 5HT2CR, ADAR1 and ADAR2 enzymes, preferably ADAR1a, ADAR1b and ADAR2 enzymes;
2) when said mammal cell is treated by a drug capable to alter the edition of the 5HT2CR,
capable of expressing of a significant number of 5HT2CR edited isoforms,
preferably capable of expressing at least one 5HT2CR isoform exhibiting at least the editing site A edited, one 5HT2CR isoform exhibiting at least the editing site B edited, one 5HT2CR isoform exhibiting at least the editing site C edited, one 5HT2CR isoform exhibiting at least the editing site D edited and one 5HT2CR isoform exhibiting at least the editing site E edited, preferably with in addition the non edited 5HT2CR isoform, when said mammal cell is treated by a drug capable to alter the edition of the 5HT2CR,
more preferably all the 5HT2CR edited and non edited isoforms are able to be expressed.

In a particular embodiment, said drug capable to alter the edition of the 5HT2CR is the interferon alpha when said cell lines have to be tested and selected for their capacity to exhibit an alteration of the 5HT2CR edition and to express or not certain 5HT2CR isoforms in presence of such a 5HT2CR drug.

In a more preferred embodiment of the methods of the present invention in step a), said mammal cells are mammal cells lines, particularly from human, mouse or rat, which exhibit a regular and constitutive expression of the 5HT2CR, ADAR1 and ADAR2 enzymes, preferably ADAR1a, ADAR1b and ADAR2 enzymes.

In a yet more preferred embodiment of the methods of the present invention in step a), said mammal cells are mammal cells lines, particularly from human, mouse or rat, having the following characteristics:
a) having a regular and constitutive expression of the 5HT2CR, ADAR1 and ADAR2 enzymes, preferably ADAR1a, ADAR1b and ADAR2 enzymes;
b)—capable of expressing of a significant number of 5HT2CR edited isoforms, preferably all of the 5HT2CR edited isoforms and, when said mammal cell is treated by a drug capable to alter the edition of the 5HT2CR; and
wherein the drug capable to alter the edition of the 5HT2CR is a drug known to present a warning from the Scientific Community or/and the Food and Drug Administration (FD) about risk of side effect in some patients having received said drug, such as psychological or neuropsychiatric side effects, this alteration which thus can be correlated to this warning.

In an even more preferred embodiment of the methods of the present invention in step a), said mammal cells are from a neuroblastoma cell line, particularly from a human neuroblastoma cell line.

In a preferred embodiment of the methods of the present invention in step a), said mammal cells are from human, mouse or rat, more preferably said mammal cells are cells from a neuroblastoma cell line, particularly from a human neuroblastoma cell line.

In a more preferred embodiment of the methods of the present invention in step a), said mammal cells are from the human neuroblastoma SH-SY5Y cell line, particularly the SH-SY5Y cell line number EC94030304 from the European Collection of Cell Cultures (ECACC).

In a preferred embodiment, in step c) of the methods of the present invention, the editing profile of each identified iso form of the 5-HT2CR mRNA and the quantitative expression of said editing enzymes ADAR1a, ADAR1b and ADAR2 are determined in the same cellular extract.

In a preferred embodiment of the methods of the present invention in step c), when the editing profile of each identified isoform of the 5-HT2CR mRNA and the quantitative mRNA expression of said editing enzymes ADAR1a, ADAR1b and ADAR2 are determined in the same cellular extract, they are determined in the same total RNA cell extract.

In a preferred embodiment of the methods of the present invention in step c), the analysis of the results of the determination of the editing profile allow to obtain the activity indexes of these editing enzymes ADAR1a, ADAR1b and ADAR2.

In a more preferred embodiment, said activity indexes of these editing enzymes are calculated by a method comprising the step of):

a) determining the mean proportion (%), preferably ±SEM (n≥3, 4, 5 and 6), of each identified isoform of the 5-HT2cR mRNA measured in the cellular RNA, or the mean proportion at least the set of iso forms corresponding to the editing sites which are chosen to be associated to the signature in step c) (A, B, C, D and/or E editing sites), or the mean proportion at least the major isoforms found in a control and/or a reference treated sample and corresponding to the editing sites which are chosen to be associated to the signature in step c) (A, B, C, D and/or E editing sites);

b) optionally, classifying these iso forms in function of the algebraic delta when compared to the control and, optionally, to a reference group, preferably to a treated group with a reference drug;

c) determining a signature associated to and significant of the activity of the editing enzymes, preferably by classification of the products of the enzymes activities, more preferably by a method which calculates and correlates the percentage of edition of at least two, preferably 3 or 4 of the editing sites selecting from the: A, B, C, D and E editing sites, more preferably by a method which calculates and correlates the percentage of edition of each of the editing sites found in each part of the signature; and d) optionally, classifying the expressed activity by measuring the % represented by all the isoforms, or by the selected iso forms, for which have been implicated ADAR 1 action (ADAR I) or ADAR2 (ADAR II).

Concerning step a), it can be chosen to evaluate only some specific editing action, for example to identify the proportion of products of the enzyme activities in which only the sites C and E have been found edited, or A and C, A and B, A and B and C, etc. The non edited isoform (NE) can be also significant and consequently chosen.

For example, when a comparison has to be done with a reference sample which has been treated with a drug, it can be chosen to evaluate only the specific editing action which have been demonstrated as being altered by this treatment, compared to control sample, and thus to identify only the proportion of the corresponding products of these specific enzyme (enzyme activities in which only the sites C and E have been found to be altered or A and C, A and B, A and B and C, etc.).

In a yet more preferred embodiment, said activity indexes of these editing enzymes are calculated from the editing isoforms due to the action of at least ADAR1 alone (ADAR1) and the action of the ADAR2 (ADAR2).

In an even more preferred embodiment, said activity indexes of these editing enzymes are calculated from the editing iso forms due to the action of ADAR1 alone and to the combined action of ADAR 1 and of ADAR 2 (ADAR1+2) and from the exclusive action of the ADAR2 (ADAR2).

In a yet more preferred embodiment, the step a) of the method for calculating said activity indexes of these editing enzymes comprises the determination of the mean proportion (%), preferably ±SEM (n≥3, 4, 5 and 6), of all the 32 iso forms of the 5-HT2cR mRNA capable of being present in the cellular RNA extract after contacting the cells with the compound to be tested.

In a preferred embodiment of the methods of the present invention in step c), the quantitative expression of said editing enzymes ADAR1a, ADAR1b and ADAR2 is determined by the measure of the mRNA expression of said editing enzymes or by the measure of said editing enzymes protein expressed in the cellular extract.

In a preferred embodiment of the methods of the present invention the potential toxicity or side-effects of said test compound to be determined is the potential risk of drug induced mood disturbance and suicide, particularly mental disorders, schizophrenia, depression, depressed suicide or abnormal feeding behaviour.

In a preferred embodiment of the methods for screening and/or selecting potential drug compound of the present invention, for treating pathology related to the alteration of the mRNA editing the 5-HTR2C after its administration, are pathologies selected from the group consisting of mental disorders, schizophrenia, depression, depressed suicide or abnormal feeding behaviour.

In a preferred embodiment of the methods of the present invention in step b) said mammals cells are cultivated in presence of the compound to be tested in a medium suitable or convenient for the culture of said mammal cells, and preferably convenient for the expression of the 5-HTR2C and the editing enzymes ADAR1 (1a and 1b) and ADAR2.

Preferably, in step b) said mammals cells are cultivated in presence of the compound to be tested for at least the time necessary to modify the expression of edited isoforms of 5HT2CR mRNA and/or the ADAR1a, ADAR1b and ADAR2 enzymes expressed, whether they can be modified by such a compound.

Preferably in step b) said mammals cells are cultivated in presence of the compound to be tested for at least 1 hour, more preferably at least 5, 10, 16, 24 and 48 hours before the step c) of determining in the same cellular extract the editing profile of each identified isoform of the 5-HT2CR mRNA and/or the quantitative expression of said editing enzymes ADAR1a, ADAR1b and ADAR2.

The methods for determining the editing steady state includes to determine the profile of each identified isoform of the 5-HT2CR mRNA measured in a cellular RNA extract involving a nested type PCR allowing the determination of the exact distribution the ADAR isoforms expressed in a cell extract and to estimate, in the same extract, the steady state of expression of the editing enzymes. They can be found also in the PCT Patent application "Peripherical tissue sample containing cells expressing the 5HTR2C and/or ADARs as markers of the alteration of the mechanism of the 5HTR2C mRNA editing and its applications" filed on Jun. 13, 2008 under the number PCT/EP2008057519 and published on Dec. 18, 2008 (WO 2008/152146).

In a preferred embodiment of the methods of the present invention in step c), the editing profile giving the mean proportion of each identified iso form of the 5-HT2CR mRNA measured in the cellular RNA extract is determined by a nested type PCR comprising two rounds of PCR, and wherein the first round of PCR is carried out by the following sets of primers:

for mouse or rat mammal cell lines:

```
                                            (SEQ ID NO. 1)
    Forward: 5'-TGTCCCTAGCCATTGCTGATATGC-3', (SEQ ID NO. 2)
    Reverse: 5'-GCAATCTTCATGATGGCCTTAGTC-3';
``` for human cell lines:

```
                                            (SEQ ID NO. 1)
    Forward: 5'-TGTCCCTAGCCATTGCTGATATGC-3', (SEQ ID NO. 2)
    Reverse: 5'-GCAATCTTCATGATGGCCTTAGTC-3';
``` and wherein the second round of PCR is carried out by the following set of primers:

for mouse or rat cell lines:

Forward: 5'-TTTGTGCCCCGTCTGGAT-3', (SEQ ID NO. 5)

Reverse: 5'-GCCTTAGTCCGCGAATTG-3'; (SEQ ID NO. 6)

and
for human cell lines:

Forward: 5'-ATGTGCTATTTTCAACAGCGTCCATC-3', (SEQ ID NO. 3)

Reverse: 5'-GCAATCTTCATGATGGCCTTA-3'. (SEQ ID NO. 4)

In a preferred embodiment of the method according to the present invention, the editing rate for each edited and unedited form of said 5HTR2C mRNA is determined by a method which comprises the following steps:

A) extraction of the total RNAs of said mammal cells, followed, where appropriate, by purification of the mRNAs;

B) reverse transcription of the RNAs extracted in step A); and

C) PCR amplification of the cDNAs obtained in step B) using at least a pair of primers specific for the 5HTR2C mRNA fragment containing the edition sites which may be edited, this pair of primers being chosen so as to be able to amplify all the editing forms and the unedited form potentially present in the RNA extract.

In a preferred embodiment of the method according to the present invention, the editing rate for each edited and unedited form of said 5HTR2C mRNA is determined by a method which comprises the following steps:

A) extraction of the total RNAs of said mammal cells, followed, where appropriate, by purification of the mRNAs;

B) reverse transcription of the RNAs extracted in step A); and

C) PCR amplification of the cDNAs obtained in step B) using at least a pair of primers specific for the 5HTR2C mRNA fragment containing the edition sites which may be edited, this pair of primers being chosen so as to be able to amplify all the editing forms and the unedited form potentially present in the RNA extract, and wherein the step B) of reverse transcription is carried out by using an oligonucleotidic primer specific of the 5HTR2C gene.

In a preferred embodiment of the method according to the present invention, in step C), the primers used in the PCR amplification step (in the second round if it is a nested type PCR) are labelled, preferably labelled with fluorophores.

In a preferred embodiment of the methods of the present invention in step c), the editing profile giving the mean proportion of each identified iso form of the 5-HT2CR mRNA is determined by an CE-SSCP method capable of providing the editing profile for each of the edited and unedited separate forms of said mRNA, said SSCP method being characterized in that it comprises after the steps A), B) and C) the following steps:

D) where appropriate, purification of the PCR products obtained in step C);

E) where appropriate, quantification of the PCR products obtained in step D);

F) dissociation of the double-stranded cDNAs to single-stranded cDNAs, in particular by heating followed by abrupt cooling;

G) separation of the single-stranded cDNAs by capillary electrophoresis; and

H) obtaining of the editing profile by reading of the fluorescence and, where appropriate, acquisition of the profile data by means of the exploitation system associated with the fluorescence reader.

In a preferred embodiment of the methods of the present invention in step c), the pair of primers specific for the ADAR mRNA PCR amplification are selected from the group consisting of:

for human ADAR1-150 isoform mRNA amplification:

Forward: 5'-GCCTCGCGGGCGCAATGAATCC-3', (SEQ ID NO. 7)

Reverse: 5'-CTTGCCCTTCTTTGCCAGGGAG-3'; (SEQ ID NO. 8)

for human ADAR1-110 isoform mRNA amplification:

Forward: 5'-CGAGCCATCATGGAGATGCCCTCC-3', (SEQ ID NO. 9)

Reverse: 5'-CATAGCTGCATCCTGCTTGGCCAC-3'; (SEQ ID NO. 10)

for human ADAR2 mRNA amplification:

Forward: 5'-GCTGCGCAGTCTGCCCTGGCCGC-3', (SEQ ID NO. 11)

Reverse: 5'-GTCATGACGACTCCAGCCAGCAC-3'; (SEQ ID NO. 12)

for mouse ADAR1-150 isoform mRNA amplification:

Forward: 5'-GTCTCAAGGGTTCAGGGGACCC-3', (SEQ ID NO. 13)

Reverse: 5'-CTCCTCTAGGGAATTCCTGGATAC-3'; (SEQ ID NO. 14)

for mouse ADAR1-110 isoform mRNA amplification:

Forward: 5'-TCACGAGTGGGCAGCGTCCGAGG-3', (SEQ ID NO. 15)

Reverse: 5'-CTCCTCTAGGGAATTCCTGGATAC-3'; (SEQ ID NO. 14)

and
for mouse ADAR2 mRNA amplification:

Forward: 5'-GCTGCACAGTCTGCCTTGGCTAC-3', (SEQ ID NO. 16)

Reverse: 5'-GCATAAAGAAACCTGAGCAGGGAC-3'. (SEQ ID NO. 17)

In a preferred embodiment of the methods of the present invention the compound to be tested is further administered in vivo to an animal model, preferably a mouse or a rat, suitable to test the same compound and wherein the potential toxicity or side-effects of this test compound after its administration in this animal model can be evaluated, particularly by evaluating the alteration of the mRNA editing of the 5HTR2C and/or the ADAR iso forms expressed in total blood and skin sample, or in brain (as disclosed in the international PCT patent application filed on Jun. 13, 2008 under the number PCT/EP2008057519 and published on Dec. 18, 2008 under the number WO 2008/152146).

In another aspect, the present invention is directed to a kit for the determination of the potential toxicity or side-effects of a test compound after its administration in a patient or for the selection of a therapeutical compounds useful for the treatment of pathology related to an alteration of the mechanism of the mRNA editing of ADAR dependent A to I mRNA editing of the 5HTR2C, said kit comprising:

a) mammal cells from a cell line wherein said cells express the editing enzymes ADAR1a, ADAR1b and ADAR2 and the serotonin 2C receptor (5HTR2C); and b) two set of primers for measuring each isoform of the 5-HT2CR mRNA which can be present in a RNA extract of said mammal cells by a CE-SSCP method involving a nested type PCR comprising two rounds of PCR; and/or c) a set of primers for measuring by a quantitative Q-PCR the quantitative expression of the editing enzymes ADAR1a, ADAR1b and ADAR2.

In a preferred embodiment of the kit of the present invention, said mammal cells are capable of expressing of a significant number of edited isoforms of 5HT2CR mRNA demonstrating that these ADAR1a, ADAR1b and ADAR2 enzymes are active to control the production of several edited isoforms of the receptor in these cells.

More preferably, these mammal cells are able to present at least the sites A, B and also C and E edited, also more preferred are mammals cells which can present at least 1, preferably 2, 3, 4, 5, 6, 7, 6, 9, 10, 11 and 12, edited ADAR 1 isoforms selected from the group consisting of A, AB, ABC, ABCE, ABE, AC, ACE, AE, B, BC, BCE, BE edited isoform, together with at least 1, preferably 2, 3, 4, 5, 6, 7, 6, 9, 10, 11, 12, 13, 14 and 15 isoforms presenting also the edited D site selecting from the group of the edited isoforms ABCD, ABCDE, ABD, ABDE, ACD, ACDE, AD, ADE, BCD, BCDE, BD, BDE, C, CE and E.

In a preferred embodiment of the kit of the present invention said mammal cells are from human, mouse or rat, more preferably said mammal cells are cells from a neuroblastoma cell line, particularly from a human neuroblastoma cell line.

In a more preferred embodiment of the kit of the present invention, said mammal cells are from the human neuroblastoma SH-SY5Y cell line.

In a particular aspect, the present invention is directed to an in vitro method for the determination or for the prediction of the potential toxicity or side-effects of a interferon alpha (IFNα) treatment after its administration in a patient, particularly for a patient infected by the HCV (Hepatitis C virus), said method comprising the following steps of:

a) obtaining a biological sample containing mammal white cells, preferably leucocytes or monocytes cells, from said treated patient;

b) determining in the cellular extract of said biological sample containing mammal white cells the quantitative expression of each of the editing enzymes ADAR1a, ADAR1b and ADAR2, and, optionally the editing profile giving the mean proportion of each identified isoform of the 5-HT2CR mRNA measured in the cellular RNA extract;

d) comparing the results obtained in step b) between said cells from said IFNα treated patient with non treated control cells or with. IFNα treated cells prior obtained from the same patient at the beginning or during the IFNα treatment.

The present invention is also directed to an in vitro method of predicting the potential toxicity of test compounds or for the selection of therapeutical compounds useful for the treatment of pathology related to an alteration of the mechanism of the mRNA editing of ADAR dependent A to I mRNA editing of the serotonin 2C receptor (5HTR2C), which comprises:

(a) screening compounds on a mammal cell line (preferably those cell lines having the characteristics depicted for the method of the present invention), preferably neuroblasto cell line, more preferably the SH-SY5Y cell line, for their ability to alter the 5HT2CR edition, these compounds being known to have or not toxicity or side-effects, such as psychologic or neuropsychologic effects;

(b) based on said screening, selecting a panel of reference members, said panel comprising members which differ with respect to their ability to alter the 5HT2CR edition and, optionally, which differ with respect to their toxicity or side-effects;

(c) screening a test compound of unknown activity relative to said 5HT2CR edition to determine its effect on the alteration on the 5HT2CR edition, thereby obtaining the edition profile of the 5HT2CR and, optionally, the ADARs expression for said test compound;

(d) comparing the edition profile of the 5HT2CR and, optionally, the ADARs expression for said test compound and for said panel of references;

(e) predicting the potential toxicity of test compounds or selecting the test compound as potential therapeutical compounds useful for the treatment of pathology related to an alteration of the mechanism of the mRNA editing 5HTR2C, based on the assumption that the alteration of the 5HTR2C edition resulting from the test compound will be similar to that of reference compound, wherein screening steps on said mammal cell line for their ability to alter the 5HT2CR profile edition and, optionally, the ADARs expression, is the same in vitro cell-based assay depicted for the method of the present invention above, as in claims 1 to 15.

The present invention finally comprises a kit according to the present invention, said kit further comprising a panel of references as selected in step b) of the above method or/and the edition profile of the 5HT2CR and, optionally, the ADARs expression for said panel of references.

The following examples and also the figures and the legends hereinafter have been chosen to provide those skilled in the art with a complete description in order to be able to implement and use the present invention. These examples are not intended to limit the scope of what the inventor considers to be its invention, nor are they intended to show that only the experiments hereinafter were carried out.

LEGEND TO THE FIGURES

Figure 1B:
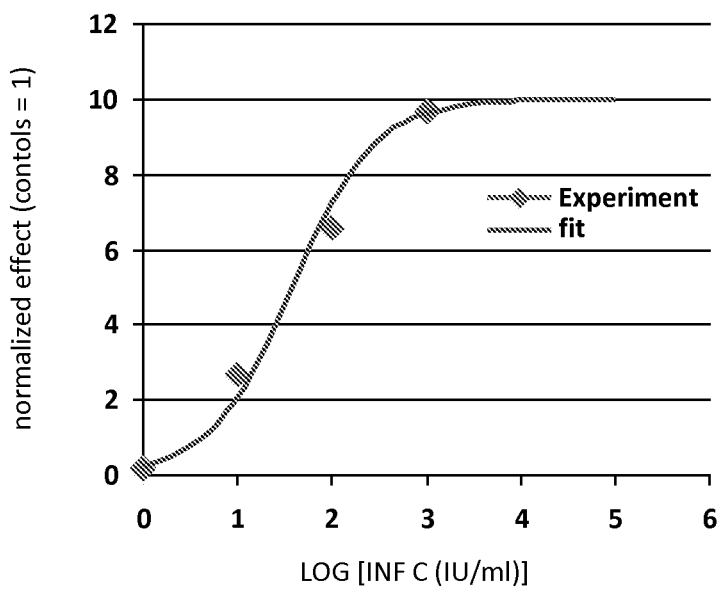

FIGS. 1A and 1B: Effect of human interferon 24 hours application on ADAR1a mRNA concentration of SH-SY5Y cells: determination of EC50%.

ADAR1a RNA Expression in SH-SY5Y cells (Q-PCR, Applied TaqMan probes ref: Hs 01020780_m1).

Reference gene: GAPDH.

Figure 2A:
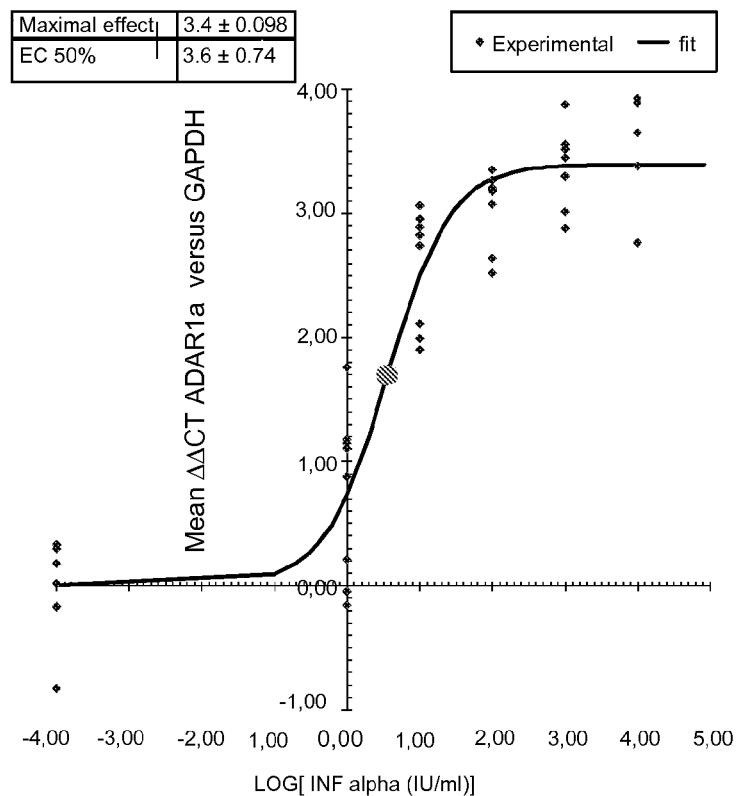
Figure 2B:
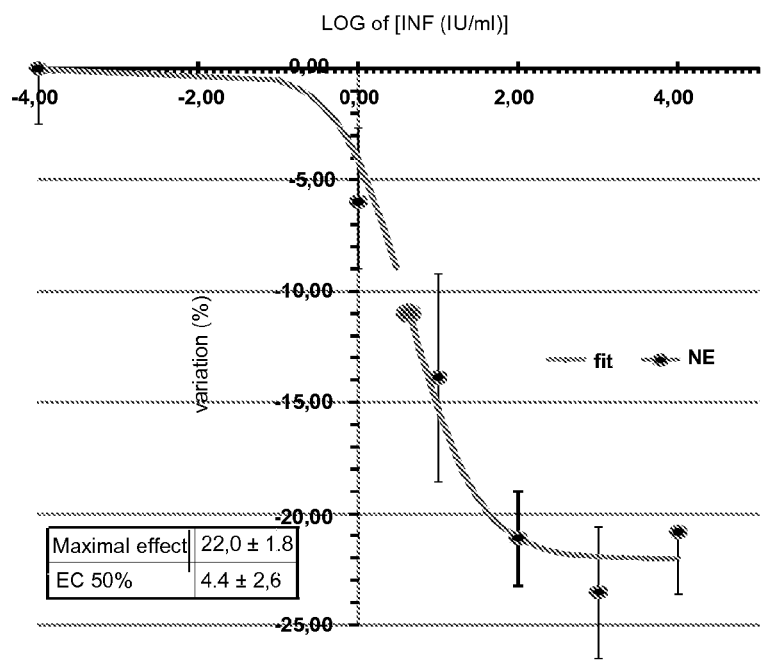
Figure 2C:
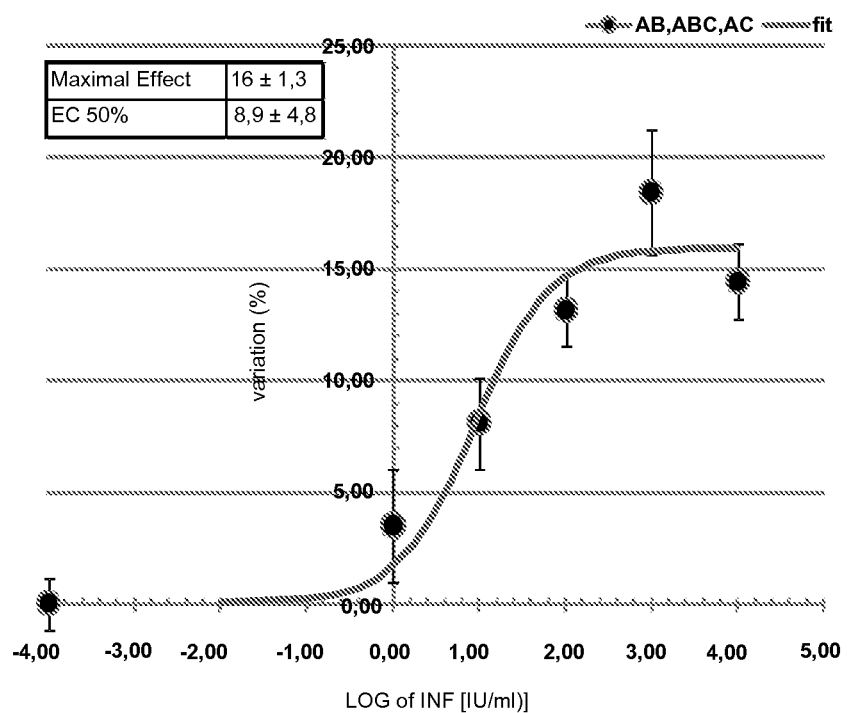

FIGS. 2A-2C: The modifications of editing profile reflect the alteration of the expression of ADAR1a in SH-SY5Y cultured cell treated by INF alpha.

FIG. 2A. The ΔΔCTs of the ADAR1a mRNA of treated dishes (n=8) versus controls (n=8) are plotted versus LOG 10 of the applied concentrations of INF α. A best fit of the hyperbolic relationship adjusted by least square method allowed to calculate the maximum effect and the IC 50% estimated as their Mean±SD (n=40).

FIG. 2B. The same experiment was done by amplification of the 5-HT2cR mRNA and the increase in the editing alteration was followed by the significant decrease of the NE iso form after identification of each individual editing profile. The results are calculated as for A from individual values (n=40).

FIG. 2C. The results concern the relationship of the positive variation of the percentage represented in the profile distribution by the sum of the 3 edited isoforms AB, ABC and AC versus the INF cc concentration. The best fit estimated the maximal effect and IC 50% from the individual values of measurements (n=40) as in A and B. The IC 50% are expressed as IU/ml of culture medium. The maximal effects determined for ADAR1a mRNA as ΔΔCT normalized to controls gives a mean calculated value of QR of 10.56 when the mean controls is normalized to 1. In FIGS. 2B and 2C the y plot correspond to the mean values of the absolute variation versus controls±SEM. The allowable error for the best fitting was 0.01%.

Figure 3:
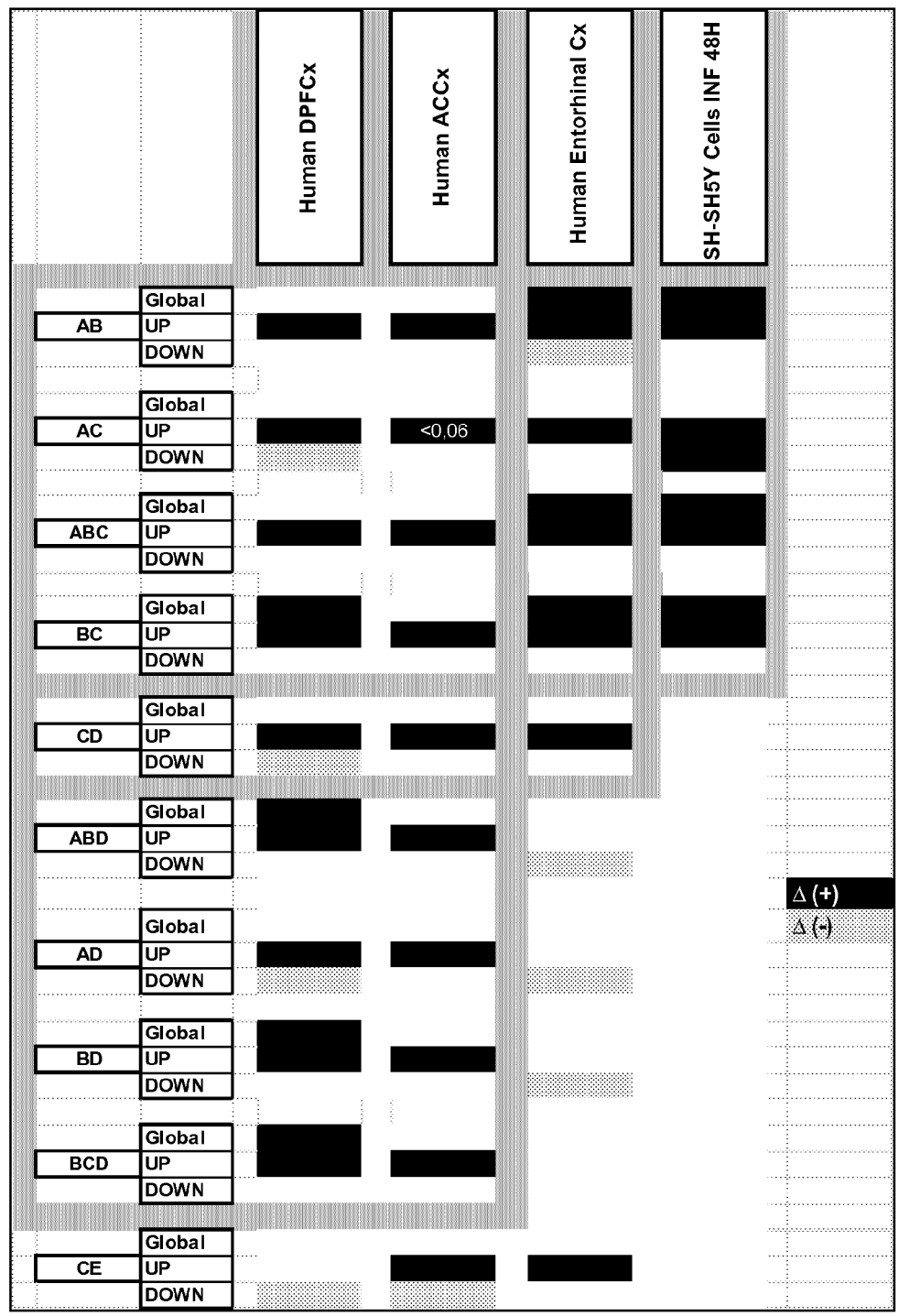

FIG. 3: A cell model as a basis to evaluate a possible psychiatric risk.

The receptor (5-HT2cR) mRNA editing <<signatures>> has been evaluated in 3 limbic cerebral structures (dorsal prefrontal (DPFCx), anterior cingular (ACCx) and entorhinal (Entorhinal Cx) cortices of depressed/suicide patients. This signature corresponded to the variations of the distribution of the respective proportions of each identified edited iso forms (see table 7) when their mean values were compared to those found in the control group of patients. They were first classified by their algebraic mean of individual delta, then treated by component statistical analysis. Each component was defined as the proportion of edited isoforms in which for example A and B sites, or A and C or A, B and C, etc. were found edited. The Black and grey rectangles respectively represent a positive and negative mean variation of the defined component when it was identified as significant (p<0.05).

Figure 4:
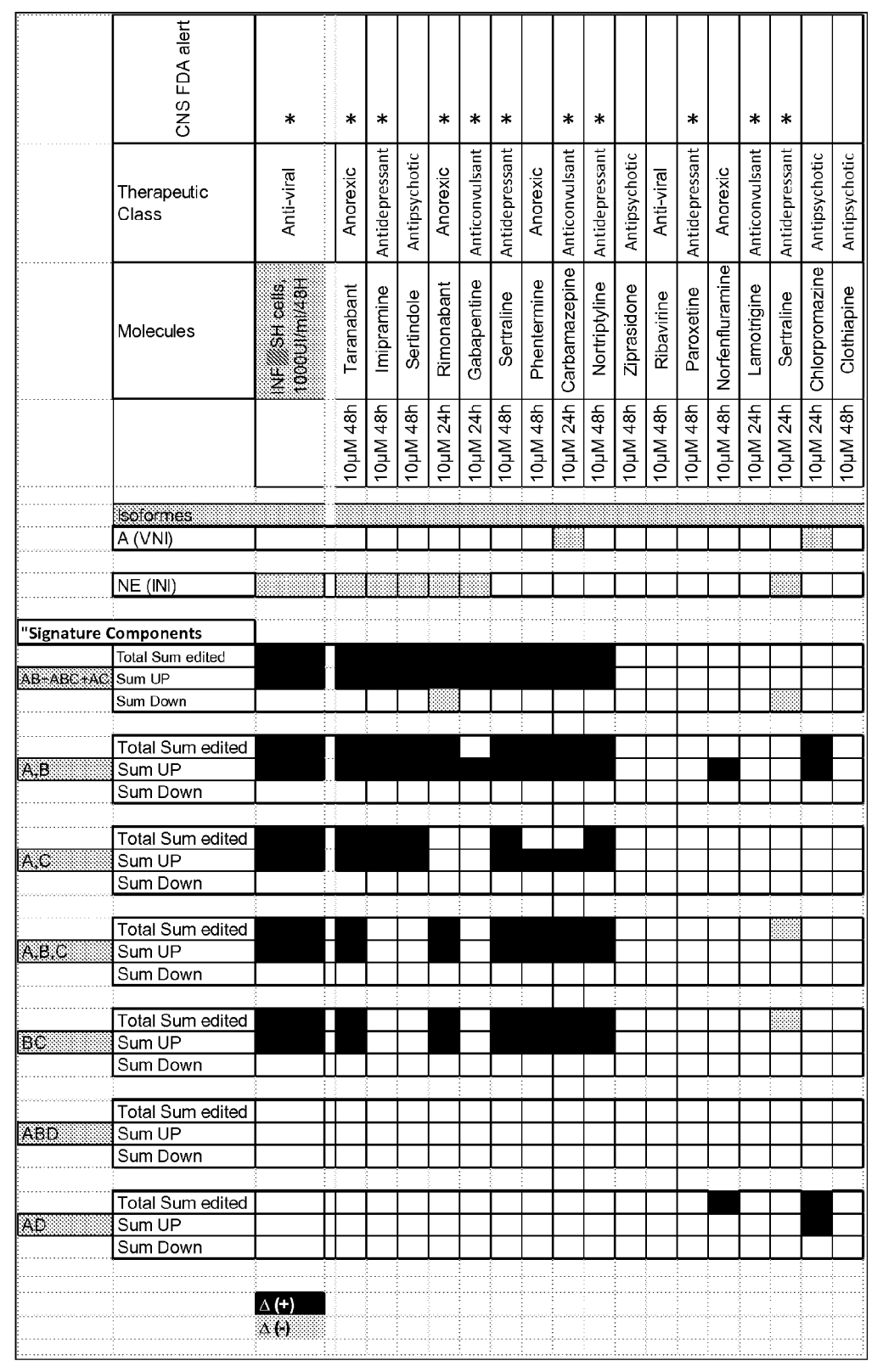

FIG. 4: Typical example of in vitro profiling of drugs by following the alteration of the activity of editing as detected from given statistical components analysis of the editing profiles of 5-HT2cR mRNA in SH-SY5Y cultured cells. For each tested molecules the components of the signature which were found significant are represented by black (positive variations) and grey (negative variations). For each component the alteration can affect the positive and/or negative parts of the signature and can be also found altering their total sum. The choice of the components is directly derived from the comparison of the analysis performed in suicide patients and INF α treated SH-SY5Y cultured cells presented in FIG. 3. The * indicates that the corresponding molecule has been the object of a FDA Psychiatric Alert for mood disturbance and suicide risk during treatment.

Figure 5:
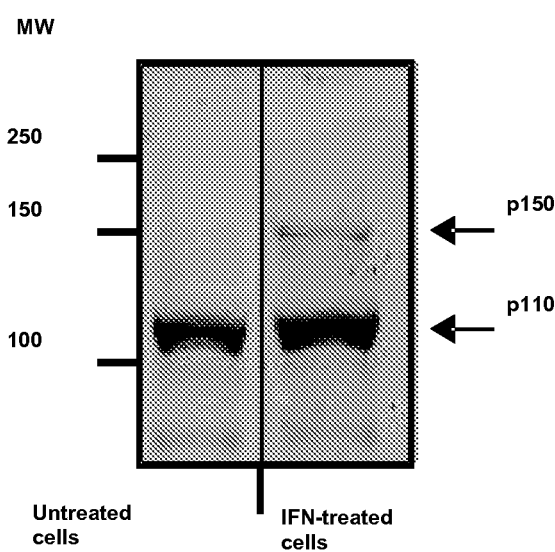

FIG. 5: ADAR1 mRNA and protein expression in IFNα-treated SH-SY5Y cells. Protein extracts SDS transferred nitrocellulose membrane. Bands corresponding to both constitutive (p110) and inducible (p150) ADAR1 isoforms are shown with arrows. Protein standards are also depicted (MW 250, 150 and 100 kD.

EXAMPLES

Example 1

Cell Culture and Pharmacological Treatment

Among ten different cell lines screening the SH-SY5Y human neuroblastoma cell line was selected as the most interesting when used in the following conditions.

The SH-SY5Y Human neuroblastoma cell line was purchased from ECACC (EC94030304 from the European Collection of Cell Cultures (ECACC)). The cell line SH-SY5Y is a thrice-cloned neuroblastoma, originally from SK-N-SH and first reported in 1978. A neuroblast-like subclone of SK-N-SH, named SH-SY, was subcloned as SH-SY5, which was subcloned again as SH-SY5Y (Biedler J L et al. Cancer Res. 1978; 38:3751-7). Cells were cultured in high glucose D-MEM medium (Sigma, ref D6546) supplemented with 10% dialysed FCS (PAA, ref. A15-507, lot A50708-0050), 2 mM Glutamine (Sigma, G7513) and a 1× mix of Antibiotic-Antimycotic Stabilized (Sigma, ref. A5955) at 37° C. under a humidified atmosphere of 5% CO2. The day preceeding drug or hIFNα treatment, SH-SY5Y cells were plated in 6-well plates at a density of $10^6$ cells/well. One 6-well plate was used per experimental condition (concentration or treatment duration). The day after plating, culture medium was removed and cells were incubated for 24 hours with a 10 μM solution of the compound to be tested molecules or a 1000 IU/ml solution of hIFNα (PBL biomedical laboratories). For hIFNα dose-response experiment cells were incubated with 1, 10, 100, and 1000 IU/ml of hIFNα solutions. For hIFNα time-course experiment cells were treated for 24, 48, or 72 hours with a 1000 IU/ml solution of hIFNα. After the different treatments, cells were directly lysed in RLT lysis buffer and total RNA purified according to manufacturer's protocol (Qiagen, RNeasy Plus mini kit, ref. 74134). Total RNA was then reverse transcribed with Thermoscript RT-PCR system Plus Taq (Invitrogen, 11146-032) and the resulting cDNA used for CE-SSCP and quantitative real-time PCR.

Example 2

In Vivo Protocol for mIFNα and Drug Treatment

For the mIFNα experiment, 8 males (Balb/cJ mice, Charles Rivers) were injected i.p route once with 10000 IU of mIFNα (PBL biomedical laboratories). Control mice were injected same route with sterile Phosphate Buffer Saline. 8 hours after injection animals were sacrificed by decapitation and total blood, ventral skin and brain collected. Total RNAs were purified with Mouse RiboPure Blood RNA Isolation kit (Ambion, ref. 1951) for blood, TRIzol reagent (Invitrogen, ref 15596-026)—after tissue disruption—for skin, and RNeasy lipid mini kit (Qiagen, ref 74804) for brain. Total RNA was then reverse transcribed with Thermoscript RT-PCR system Plus Taq (Invitrogen, 11146-032) and the resulting cDNA used for CE-SSCP and quantitative real-time PCR. The method used for SSCP determinations was already described for mouse and human samples (see patent PCT/EP 2008/057519 filed on Jun. 13, 2008).

For antipsychotic, antidepressant, and suicide warning drugs, the different compounds were first dissolved in the vehicle (DMSO/Ethanol/Water: 50%/15%/35%) and administered to male Balb/cJ mice through Alzet pumps (Alzet, ref. 2002, ordered from Charles River, France) to have a continuous and homogenous drug delivery. The Control group was composed of 8 mice treated with the vehicle alone. The test groups were composed of 8 mice treated with compounds at a dose of 3.5 or 7.0 mg/kg/day dissolved extemporaneously in the vehicle. After 15 days of drugs delivery through Alzet pumps animals were sacrificed by decapitation. As previously described samples of total blood and skin, and brain were collected. Total RNA were purified and reverse transcribed as mentioned above.

Example 3

Total Profile of Distribution of all the Expressed Edited and Non Edited Isoforms of the 5-HT2cR mRNA; Quantification of 5-HT2cR (Total) and ADARs mRNA Expression by Real-Time PCR Analysis 3a) Total Profile of Distribution of all the Expressed Edited and Non Edited Iso Forms of the 5-HT2cR mRNA by Non Denaturing Capillary Electrophoresis by Single Strand Conformational Polymorphism (CE-SSCP) (See Also International PCT Patent Application WO 2008/152146, Example 2 and FIG. 1)

a): Obtention of the Complete Editing Profile from One Sample of Brain Tissue

Total RNA was extracted and purified from tissue or cell extracts, according to manufacturer's specifications (Qiagen RNeasy, Mini Kit). The quantity and purity of the extracted RNA were assessed by measuring both the absorbance at 260 nm and the 260/280 nm ratio with a GeneQuant spectrophotometer (PharmaciaBiotech). In order to eliminate possible contamination by genomic DNA, 8 µl of each RNA (between 88 ng and 1.3 µg) were then treated with 1 unit of DNase I (Invitrogen) for 15 min at room temperature in a final volume of 10 µl. The reaction was stopped by adding 1 µl of 25 mM EDTA and then heated for 10 min at 65° C. The reverse transcription of DNAse I-treated RNAs (10 µl) was performed using 15 units of ThermoScript reverse transcriptase (ThermoScript RT-PCR System, Invitrogen) and Oligo(dT) primers at a final concentration of 2.5 µM.

A first PCR reaction (final volume 25 µl) resulting in a 250 bp fragment, was then carried out on 1 µl of the reverse transcription products with 0.2 unit of Platinum Taq DNA polymerase (ThermoScript RT-PCR system, Invitrogen) and specific primers (forward primer: 5'-TGTCCCTAGCCATTGCTGATATGC-3' (SEQ ID No. 1) and reverse primer: 5'-GCAATCTTCATGATGGCCTTAGTC-3' (SEQ ID No. 2); final concentration of each 0.2 µM) located on exon IV and exon V of the Human 5-HT2cR cDNA, respectively. After a denaturing step at 95° C. for 3 min, the PCR was brought to its final point after 35 cycles (15 s at 95° C.; 30 s at 60° C.; 20 s at 72° C.), and a final elongation step of 2 min at 72° C. Aliquots of the amplification products were used to check the product on a 2% agarose analytic gel.

b) Second PCR and Separation of Single-Strand cDNA Fragments by Capillary Electrophoresis (CE)

1 µl of a 1/50 dilution of the RT-1$^{st}$ PCR products, or the 250 bp cDNA amplified from plasmids harboring the thirty-two standard of human 5-HT2cR (or 5HT2CR) isoforms, were used as templates for an additive nested-PCR. These 32 standards, corresponding to the non-edited (NE) and edited isoforms of human 5-HT2cR. Amplifications were performed in a final volume of 20 µl with HPLC-purified fluorescent primers (forward primer: FAM-ATGTGCTATTTTCAA-CAGCGTCCATC-3' (SEQ ID No. 3); reverse primer: VIC-GCAATCTTCATGATGGCCTTA-3' (SEQ ID No. 4); final concentration of each 0.2 µM), and 0.2 unit of Platinum Pfx DNA polymerase (Invitrogen).

The VIC-labelled reverse primer hybridizes to a complementary sequence of the 5-HT2c receptor identical in human, mouse and rat. On the other hand, although used with human samples, the sequence of the FAM-labelled forward primer was designed to be as close as possible to that of the mouse. More precisely, T residues in positions 5 and 6 of the human oligonucleotide sequence (positions 1133 and 1134 of human reference U49516) were changed into G and C, respectively.

Simulations of stochastic folding pathways of both strands of the PCR product obtained with the two primers described above were carried out with the Kinefold server (kinefold.curie.fr). They showed that the lowest free-energy structures obtained for forward and reverse strands—the edited region embedded in the loop of a stem-loop structure, and able to hybridize with a complementary sequence located elsewhere in the whole structure after folding of the stem—were very close to that calculated for a mouse nested-PCR product successfully used for Mouse samples. This set of primers was shown to be optimal for conformational analysis of human 5HTR2C mRNA editing by non denaturing capillary electrophoresis by single strand conformational polymorphism (CE-SSCP).

The amplified fragment is 127 bp-long. As for RT-PCR, after an initial denaturing step of 5 min at 94° C., the amplification reaction was brought to an end with 35 cycles (15 s at 94° C.; 30 s at 55° C.; 20 s at 68° C.) and a final elongation step of 2 min at 68° C. Again, quality of the 127 bp-long amplified fragments were assessed on a 2% agarose gel before subsequent analysis in a 3100 Avant Genetic Analyser (Applied Biosystem).

Fluorescent PCR products corresponding to standard isoforms (1 µl of a 1/100 dilution in DEPC treated water) and samples (1 µl of a 1/30 dilution) diluted in 11 µl of deionized formamide were added to a mixture of ROX labelled migration standards (MWG-BIOTECH, AG) (0.5 µl each) covering the whole range of the electrophoregram retention times. These ROX standards were used for CE calibration and subsequently to obtain correct superimposition of standards and samples peaks. After denaturing for 2 min at 95° C., samples were immediately chilled on ice. Non-denaturing CE was carried out in an ABI PRISM 3100-Avant Genetic Analyser (Applied Biosystems) through 80-cm-long capillaries filled with 7% "POP Conformational Analysis Polymer" (Applied Biosystems), 1×TBE and without glycerol. After a pre-run performed at 15 kV for 3 min, samples were injected for 15 s at 2 kV, and electrophoresis was run for 105 min at 15 kV at a controlled temperature of 20° C. Under these conditions, each of the thirty-two possible isoforms were clearly resolved as a result of the single ssDNA conformation obtained with either the FAM-labelled or the VIC-labelled strand. The different retention times were used for unambiguous identification of the isoforms.

c) Identification and Relative Quantification of Each Isoform in Each Brain Sample The Electrophoretic Signal was then processed using an in-house software. First, the time basis of electrophoretic profiles of each sample was adjusted using the ROX-labelled strands of the migration standards. This allowed FAM- and VIC-labeled strands to precisely deconvolute the standards and samples signals in a unique time basis. Background was then adjusted and subtracted and then total area under each signal normalized.

The relative proportion of each iso form was processed by a best fitting of each deconvoluted and normalized analytical signal of the brain samples. It was performed by the iterative adjustment of the integrated signal represented by the 32 similarly deconvoluted and normalized standard analytical signals. The calculation was based on the hypothesis that the SSCP signal $$S(t) = \sum_{i=1}^{N} g_i R_i(t)$$

in which $R_i(t)$, with $i \in \{1, \ldots, N\}$, are the standard signals and $g_i$ the % of each of them in the signal. The best fit minimized the sum of squares due to error (SSE)

$$SSE = \int \left[ S(t) - \sum_{i=1}^{N} g_i R_i(t) \right]^2$$

and was controlled by the least square statistical analysis.

The result of this best fitting was statistically evaluated after calculation of the $r^2$ value such as $$r^2 = 1 - \frac{SSE}{SSM}$$

in which SSM is the Sum of Square about Mean such as $$SSM = \sum_{i=1}^{t} (S(t) - \overline{S})^2.$$

The maximum theoretical best fit would give an $r^2=1$.

All experiments were carried out under blind conditions and all samples were assayed in the same batch for RT-PCR and second PCR reactions. The best fitting results yielded a specific editing profile for each individual sample, which was determined by the percentage of each edited and non edited form of the total analytical signal. These initial values were used for statistical analyses.

This method gives the proportion of each expressed mRNA iso form expressed as the percentage of the total of 5-HT2c receptor present in the extract.

3B) Quantification of 5-HT2CR and ADARs mRNA Expression by Real-Time PCR Analysis In order to quantify levels of 5-HT2CR, ADAR1 and ADAR2 mRNA expression in SH-SY5Y cells or in prefrontal cortex, total blood and skin of Balb/cJ mice, first-strand cDNA was synthesized by reverse transcription and subjected to TaqMan quantitative real-time PCR analysis (Applied Biosystems). All probes and primers used for the quantitative PCRs were from Applied Bio systems (Gene Expression Assays, Assay-On-Demand) (see Table 1, Applied Biosystems primers and probes references):

These probes and primers could be easily designed, whether it is necessary, by the skilled person in view of the well known and disclosed nucleic sequences of the human and mouse gene encoding the 5-HT2cR, ADAR1, constitutive and inducible iso forms, and ADAR protein.

TABLE 1

|  | 5-HT2cR | ADAR1 constitutive isoform or total | ADAR1 inducible isoform | ADAR2 |
| --- | --- | --- | --- | --- |
| Balb/cJ mice | Mm 00434127_m1 | Mm 00508001_m1<br>Mm 00507998_m1 | Mm 00507997_m1 | Mm 00504621_m1 |
| Human tissues And SH-SY5Y cells | Hs 00968672_m1<br>Hs 00968671_m1 | Hs 01017596_m1 | Hs 01020780_m1 | Hs 00210562_m1 |

Human GAPDH (product no. 4326317E; Applied Biosystems) or mouse GAPDH (product no. 4352339E; Applied Biosystems) were included in each multiplex PCR as an internal control. Real-time PCR and subsequent analysis were performed with a 48-well block StepOne RT PCR system (Applied Biosystems). Quantification of target gene expression in all samples was normalized to GAPDH expression by the equation Ct (target)−Ct (GAPDH)=ΔCt, where Ct is the threshold cycle number. The mean ΔCt value of samples from untreated mice or cells was determined and used as a reference point for the samples corresponding to treated animals or cells. Differences between untreated and treated animals or cells, including individual variation were calculated by the equation (ΔCt (individual treated samples)−ΔCt (mean of untreated samples)=ΔΔCt). Changes in target gene expression (n-fold) in each sample were calculated by $2^{-\Delta\Delta Ct}$, from which the means and standard deviations (SD) were derived.

In order to improve the sensitivity of the selected cell line to detect a significant alteration of the editing process the process was applied to the evaluation of human interferon and of 17 molecules on which FDA had concentrated the warning Box.

Example 4

Relation Concentration-Effect on the Expression of ADAR1a of the Human Interferon Applied on SH-SY5Y Cells During 24 Hours (See FIGS. 1a and 1b)

The concentration of 1000 IU/ml was chosen for additional evaluation of the distribution of edited iso forms in controls and interferon treated cells the result is presented on Table 2.

TABLE 2

Analysis of the editing profile obtained after 24 hours of treatment by 1000 IU of human interferon alpha.

| | Editing Profile | | | | Signature | | |
|---|---|---|---|---|---|---|---|
| Isoforms | Ctls | SEM | IFN 1000 UI | SEM | Isoforms | Δ % | Student |
| NE (INI) | 54.6 | 1.9 | 37.5 | 3.5 | ADE (VDV) | −89.2 | 0.00002 |
| A (VNI) | 29.5 | 1.3 | 32.3 | 2.5 | ABCD (VSV) | −82.4 | 0.21792 |
| B (MNI) | 3.4 | 0.3 | 3.5 | 0.8 | BD (MNV) | −75.9 | 0.00002 |
| C (ISI) | 2.5 | 0.5 | 2.2 | 0.4 | BCE (MGI) | −69.2 | 0.12449 |
| AB (VNI) | 1.8 | 0.8 | 2.9 | 0.9 | ABD (VNV) | −60.5 | 0.13164 |
| ACE (VGI) | 1.4 | 0.3 | 0.8 | 0.2 | D (INV) | −59.8 | 0.00221 |
| D (INV) | 1.3 | 0.2 | 0.5 | 0.1 | CE (IGI) | −43.9 | 0.34397 |
| BD (MNV) | 1.1 | 0.1 | 0.3 | 0.1 | ABDE (VDV) | −41.7 | 0.36296 |
| AC (VSI) | 0.9 | 0.6 | 13.5 | 3.4 | ACE (VGI) | −40.2 | 0.07315 |
| AE (VDI) | 0.6 | 0.4 | 1.1 | 0.3 | NE (INI) | −31.3 | 0.00082 |
| ABD (VNV) | 0.4 | 0.1 | 0.2 | 0.2 | DE (IDV) | −28.3 | 0.06225 |
| ADE (VDV) | 0.4 | 0.0 | 0.04 | 0.0 | C (ISI) | −14.2 | 0.28715 |
| DE (IDV) | 0.4 | 0.0 | 0.27 | 0.0 | B (MNI) | 2.6 | 0.46177 |
| AD (VNV) | 0.3 | 0.2 | 1.40 | 0.5 | A (VNI) | 9.5 | 0.17352 |
| ABE (VDI) | 0.2 | 0.2 | 0.29 | 0.1 | ABE (VDI) | 25.8 | 0.40553 |
| BE (MDI) | 0.2 | 0.1 | 0.76 | 0.7 | AB (VNI) | 63.7 | 0.18693 |
| CE (IGI) | 0.2 | 0.2 | 0.13 | 0.1 | AE (VDI) | 69.2 | 0.17984 |
| ABC (VSI) | 0.2 | 0.1 | 1.62 | 0.3 | CD (ISV) | 123.2 | 0.24804 |
| ABCD (VSV) | 0.1 | 0.1 | 0.03 | 0.0 | BE (MDI) | 228.5 | 0.24235 |
| CD (ISV) | 0.1 | 0.0 | 0.19 | 0.1 | AD (VNV) | 342.7 | 0.03539 |
| BCE (MGI) | 0.1 | 0.0 | 0.02 | 0.0 | ABC (VSI) | 758.7 | 0.00104 |
| ABDE (VDV) | 0.1 | 0.1 | 0.04 | 0.0 | AC (VSI) | 1324.2 | 0.00235 |
| | 100 | | 100 | | | | |

| | Signature | | | | | |
|---|---|---|---|---|---|---|
| | Ctls | SEM | IFN 1000 UI | SEM | Δ % | Student |
| | Global signature | | | | | |
| NE (INI) | 54.6 | 1.9 | 37.5 | 3.5 | −31.3 | 0.0008 |
| Sum of Delta > 0 | 37.3 | 1.9 | 57.5 | 3.5 | 54.2 | 0.0002 |
| Sum of Delta < 0 | 8.1 | 0.4 | 4.5 | 0.5 | −44.3 | 0.0001 |
| | Edited sites | | | | | |
| | Delta > 0 | | | | | |
| A | 33.6 | 2.1 | 53.6 | 3.9 | 59.3 | 0.0006 |
| B | 5.8 | 0.7 | 9.1 | 1.6 | 56.6 | 0.0447 |
| C | 1.2 | 0.6 | 15.8 | 3.6 | 1191.6 | 0.0013 |
| D | 0.4 | 0.2 | 2.0 | 0.6 | 409.8 | 0.0125 |
| E | 1.1 | 0.6 | 2.2 | 0.6 | 99.4 | 0.1233 |
| | Delta < 0 | | | | | |
| A | 2.4 | 0.4 | 1.1 | 0.4 | −54.1 | 0.0224 |
| B | 1.8 | 0.3 | 0.5 | 0.2 | −71.3 | 0.0014 |
| C | 4.3 | 0.6 | 3.2 | 0.5 | −27.2 | 0.0793 |
| D | 3.9 | 0.2 | 1.4 | 0.3 | −64.9 | 0.0000 |
| E | 2.5 | 0.3 | 1.3 | 0.3 | −46.9 | 0.0083 |
| | Total | | | | | |
| A | 36.1 | 2.3 | 54.7 | 3.9 | 51.7 | 0.0011 |
| B | 7.7 | 0.8 | 9.6 | 1.7 | 25.8 | 0.1596 |
| C | 5.6 | 0.8 | 18.9 | 3.6 | 240.1 | 0.0022 |
| D | 4.3 | 0.4 | 3.4 | 0.6 | −20.6 | 0.1098 |
| E | 3.6 | 0.7 | 3.5 | 0.6 | −2.6 | 0.4621 |

TABLE 2-continued

Analysis of the editing profile obtained after 24 hours of treatment by 1000 IU of human interferon alpha.

| Signature | Ctls | SEM | IFN 1000 UI | SEM | Δ % | Student |
|---|---|---|---|---|---|---|
| Enzyme activity index A | | | | | | |
| Delta > 0 | | | | | | |
| ADAR1+ | 36.9 | 2.0 | 56.0 | 3.1 | 51.6 | 0.0002 |
| ADAR1 + 2+ | 0.3 | 0.2 | 1.8 | 0.6 | 485.6 | 0.0181 |
| ADAR2+ | 0.1 | 0.0 | 0.2 | 0.1 | 123.2 | 0.2480 |
| NE | | | | | | |
| Delta < 0 | | | | | | |
| ADAR1− | 1.5 | 0.2 | 0.9 | 0.2 | −41.5 | 0.0552 |
| ADAR1 + 2− | 4.9 | 0.5 | 2.8 | 0.3 | −42.1 | 0.0021 |
| ADAR2− | 1.7 | 0.2 | 0.8 | 0.1 | −52.9 | 0.0005 |
| NE | 54.6 | 1.9 | 37.5 | 3.5 | −31.3 | 0.0008 |
| Sum | | | | | | |
| ADAR1 | 38.4 | 2.1 | 56.8 | 3.0 | 48.1 | 0.0003 |
| ADAR1 + 2 | 5.2 | 0.3 | 4.7 | 0.8 | −10.2 | 0.2604 |
| ADAR2 | 1.8 | 0.2 | 1.0 | 0.2 | −44.7 | 0.0052 |
| NE | 54.6 | 1.9 | 37.5 | 3.5 | −31.3 | 0.0008 |
| Enzyme activity index B | | | | | | |
| Delta > 0 | | | | | | |
| ADARI+ | 37.2 | 1.9 | 57.8 | 3.5 | 55.3 | 0.0002 |
| ADARII+ | 0.4 | 0.2 | 2.0 | 0.6 | 409.8 | 0.0125 |
| NE+ | | | | | | |
| Delta < 0 | | | | | | |
| ADARI− | 6.4 | 0.5 | 3.7 | 0.5 | −42.0 | 0.0016 |
| ADARII− | 6.6 | 0.4 | 3.6 | 0.3 | −44.9 | 0.0001 |
| NE− | 54.6 | 1.9 | 37.5 | 3.5 | −31.3 | 0.0008 |
| Sum | | | | | | |
| ADARI | 43.6 | 2.0 | 61.5 | 3.6 | 41.1 | 0.0007 |
| ADARII | 7.0 | 0.3 | 5.7 | 0.7 | −19.1 | 0.0487 |
| NE | 54.6 | 1.9 | 37.5 | 3.5 | −31.3 | 0.0008 |

The editing profile gives the mean proportion (%) ± SEM (n = 6) of each identified isoform of the 5-HT2cR mRNA (=100%) measured in the cellular RNA. These isoforms are classified in function of the algebraic delta when compared are the control and the INF treated groups. The obtained signature is tested for significance and a multiple evaluation of the activity of the editing enzymes is then proposed by classifications of the products of the enzymes activities. The first classification (edited sites) calculates the percentage of edition of each of the editing sites: A, B, C, D and E, found in each part of the signature. When the total distribution is used, the result given in "total" corresponds in fact to a result which could be obtained by the primer extension method. The enzyme indexes were calculated from the editing isoforms due to the action of ADAR1 alone (ADAR1), to the combined action of ADAR1 and of ADAR2 (ADAR1 + 2), from the exclusive action of the ADAR2 (ADAR2). A final classification expressed the activity by measuring the % represented by all the isoforms for which have been implicated ADAR1 action (ADARI) or ADAR2 (ADARII). Other classifications are also possible (not shown here) for the evaluation of some specific editing action (for example to identified the proportion of products of the enzyme activities in which the sites C and E have been found edited, or A and C, A and B, A and B and C etc.). It is interesting to note that the non edited isoform (NE) is also significantly reduced.

It is clear that the INF treatment induces a strong and significant alteration of the editing profile which indicates that as expected demonstrates an important increase in the ADAR 1 activity and a decrease in the ADAR2 activity.

In the same samples the level of expression of the ADARs were measured by QPCR and the results are summarized on the following Table 3 and compared to those obtained after evaluation of the editing profile.

The next table summarizes the result after similar experiences performed with the same protocol to determine the eventual alteration of editing after application for 24 hours of 10 micromolar concentrations of 17 molecules which has been indicated by FDA alertness as presenting a risk of suicide induction when chronically used. These molecules belong to several chemical and different families. However they present a significant alteration of editing of 5-HT2cR. 11

TABLE 3

Comparison of expression and activity indexes of ADAR1 and ADAR2 enzymes after INF treatment of the selected cell line.

| | ENZYME ACTIVITY INDEX (% Δ) | | | | | Q-PCR (% Δ) | | |
|---|---|---|---|---|---|---|---|---|
| | ADAR1 | ADAR1 + 2 | ADAR2 | ADARI | ADARII | NE | ADAR1a | ADAR1b | ADAR2 |
| IFN 24 H | 48.05* | −10.25 | −44.75* | 41.07* | −19.08 | −31.30* | 970* | 0 | 68 |

The results are given in % of variation versus controls (n = 6). The asterisk marked (*) area and bold numbers indicate a significant variation (p < .05).

of these molecules present a significant alteration of the expression of editing enzymes. The others induce significant changes in the activity of these enzymes which can be easily detected by using the same cellular samples (see Table 4).

wells of 6-well plates were used per experimental condition (control, concentration or treatment duration). The day after plating, culture medium was removed and cells were incubated for 24 or 48 hours with a 10 µM solution of the to be

TABLE 4

The molecules indicated as presenting a suicide risk by the FDA significantly alter the editing enzymes expression and/or their editing action on 5-HT2cR mRNA. This can be easily detected by their application on a dedicated cell line (SH-SY5Y).

| | ENZYME ACTIVIY INDEX (% of variation) | | | | | | | QPCR: RNA expresion (% of variation) | | |
|---|---|---|---|---|---|---|---|---|---|---|
| | ADAR1 | ADAR1 + 2 | ADAR2 | NE | ADARI | ADARII | EC | ADAR1a | ADAR1b | ADAR2 |
| Fenfluramine | 4.2 | −43.3* | 0.7 | 4.5 | −4.8 | −34.8* | | 7 | 23 | 27 |
| Rimonabant | 13.3 | 2.4 | −3.7 | −10.4 | 11.3 | 1.2 | | −43* | −32* | −7 |
| Carbamazepine | −3 | 38.8* | 26 | −3.8 | 3 | 36.4* | | 52* | −62* | −42* |
| Felbamate | 6.3 | −13.9 | −24.6 | −1.2 | 2.4 | −16 | | −13 | −1 | 1 |
| Gabapentin | 19.2 | −28.5 | −26.7 | −8.3 | 10.1 | −28.1* | | −42* | −34* | −21* |
| Lamotrigine | 5.9 | −24.6 | −23 | 0.9 | 0.1 | −24.3 | | −26 | −26* | −32 |
| Levetiracetam | 12 | −36.6* | 10.9 | −3.1 | 2.8 | −27.4 | | −9 | −11 | −17 |
| Oxcarbazepine | 1.1 | −25.6 | −25.9 | 4.8 | −3.9 | −25.6 | −65.2* | −28 | −18 | −15 |
| Pregabalin | 2.5 | −8.7 | −6.2 | −0.1 | 0.4 | −8.2 | | −33 | −43* | −36 |
| Topiramate | 14.4 | −19.5 | 11.4 | −8 | 8 | −13.5 | | −44* | −46* | −60* |
| Zonisamide | 11.9 | 9.7 | −7.8 | −10.5 | 11.5 | 6.3 | | −24* | −19* | −23 |
| Bupropion | −16.3* | 42.6 | 68.9 | 5.3 | −8.9* | 34.7 | | −66* | −51* | −40* |
| Citalopram | −5.7 | 70.2* | 70.1* | −7.4* | 5.3 | 70.2* | | −18 | −2 | 64* |
| Desipramine | −8.6 | 5.7 | 15.5 | 5.9 | −6.6 | 7.5 | | 29 | −38 | −12 |
| Imipramine | −11.6* | 146.4* | 62.5 | −13* | 11.3 | 130.4* | | 34 | 0 | 111* |
| Trazodone | 0 | 89.3* | 28.4 | 13.4 | 12.9 | 77.7 | | −60 | −40 | 5 |
| Olanzapine | −23.2 | 84.9* | 9.2 | 7 | −7.6 | 70.5* | | −54* | 20 | 92* |

It becomes obvious that the dedicated cell line, when observed with the set of techniques allowing a rapid and complete measurement of these parameters represent a new model for the pre-clinical evaluation of the eventual risk of these molecules to produce altered mood by a chronic alteration of the 5-HT transmission.

Example 5

Choice of a Cell Line for In Vitro Predictive Effect of Molecules a—Criteria for Selection.

To be eligible for the in vitro screening of molecules the cell line must validate the main following points:
  to be from Human origin;
  to express the 5-HT2cR receptor at a range allowing a reproducible evaluation of the editing profile in control conditions;
  to express the editing enzymes in relative steady states similar to those observed in normal cortical structures in the Human brain.

b—A Proposal for a Best Choice.

Among ten different cell lines, the SH-SY5Y Human neuroblastoma cell line was selected as the most interesting when used in the following conditions.

The SH-SY5Y Human neuroblastoma cell line was purchased from ECACC. Cells were cultured in high glucose D-MEM medium (Sigma, ref. D6546) supplemented with 10% dialysed FCS (PAA, ref. A15-507, lot A50708-0050), 2 mM Glutamine (Sigma, ref. G7513) and a 1× mix of Antibiotic-Antimycotic Stabilized (Sigma, ref. A5955) at 37° C. under a humidified atmosphere of 5% CO2. The day preceeding hIFNα or drug treatment, SH-SY5Y cells were plated in 6-well plates (Corning, Multiwell Plate, 6 well, Corning Cell-BIND Surface, ref 3335) at a density of 5; 7 or 9·10$^6$ cells/well for a 72-, 48- or 24-hour treatment respectively. Six or eight tested molecules or a 1000 IU/ml solution of hIFNα (PBL biomedical laboratories). For hIFNα dose-response experiment, cells were incubated with 1, 10, 100, 1000, or 10000 IU/ml of hIFNα solutions. [For hIFNα time-course experiment cells were treated for 24, 48 or 72 hours with a 1000 IU/ml solution of hIFNα. In the case of the 72-hour treatment points, medium was changed for both controls and hIFNα-treated cells after 48 hours of culture]. Cells were then directly lysed in RLT lysis buffer and total RNA purified according to manufacturer's instructions (Qiagen, RNeasy Plus mini kit, ref. 74134). Total RNA was then reverse-transcribed with Thermoscript RT-PCR system Plus Taq (Invitrogen, ref 11146-032) and the resulting cDNA used for CE-SSCP and quantitative real-time PCR.

When possible, total protein extracts were also prepared for western-blotting. Briefly, cells from eight wells corresponding to control or treatment procedures, were lysed in 600 µl of RIPA buffer (150 mM NaCl, 10 mM Tris-HCl pH8, 5 mM EDTA, 1% Triton X100, 0.1% sodium deoxycholate) supplemented with 1 mM PMSF and Complete Mini protease inhibitor cocktail (Roche, ref. 11836153001). Cell lysates were sonicated 3×15 seconds on ice, rocked for at least 2 hours at 4° C. and then spun at 100 g for 10 min at 4° C. Insoluble pellets were resuspended in 40 µl of 2× Laemmli loading buffer and protein concentrations were quantified with a Quant-IT Protein Assay kit (Invitrogen, ref. Q33211). After sonication and denaturation for 5 min at 70° C., 75 µg of insoluble protein extracts in Laemmli buffer were loaded on a 12% denaturing polyacrylamide gel. Migration and electrotransfer of protein extracts were further performed according to standard procedures. For ADAR1 proteins detection (both constitutive and inducible forms), nitrocellulose membranes were blotted with a L-15 affinity purified goat polyclonal antibody (Santa Cruz, ref. sc-19077).

c—Steady State of the Expression Editing Enzymes and 4-HT2cR in SH-SY5Y in Control Conditions.

It is illustrated on the table 5.

TABLE 5

| RNA Origin | RQ ADAR1a | RQ ADAR1b | p | RQ ADAR2 | p | RQ 5-HT2cR | p |
|---|---|---|---|---|---|---|---|
| SH-SY5Y cells | 1 | 48.10 | <0.0001 | 1.78 | 0.02 | 0.02 | <0.0001 |
| Pool of cortex RNAs | 1 | 40.19 | <0.0001 | 0.24 | 0.000889 | 1.31 | 0.044 |
| HTB-14 cells | 1 | 20.27 | <0.0001 | 4.23 | 0.000018 | | |

Relative expression of ADAR1a, ADAR1b, ADAR2 and 5-HT2cR mRNA in the SH-SY5Y neuroblastoma, and HTB-14 astrocytoma cell lines and in a pool of Human brain, cerebral cortex total RNA. Cells lines were purchased from ECACC (SH-SY5Y, ref. 94030304) and ATCC (HTB-14, ref. HTB-14). Cerebral cortex total RNA was purchased from Clontech (ref. 636561). Quantification of mRNA levels of expression was performed by TaqMan quantitative real-time PCR analysis (Q-PCR) on a Applied Biosystems StepOnePlus ™96-well apparatus (Applied Biosystems, ref. 4376592). All probes and primers used for Q-PCR were from Applied Biosystems (Gene Expression Assays, Assay-On-Demand): 5-HT2cR (Hs 00968672_m1), ADAR1 p110 constitutive isoform (Hs 01017596_m1), ADAR1 p150 inducible isoform (Hs 01020780_m1), ADAR2 (Hs 00210562_m1). Human GAPDH (Applied Biosystems, ref. 4326317E) was included in each multiplex Q-PCR as an internal control. RQ (Relative Quantitation) were calculated as described by the furnisher. In each tissue or cell line, expression of the ADAR1a gene was taken as a reference and its RQ equal to 1.

It is important to note that when compared with the ADAR1a isoform (taken here as reference) which is the inducible iso form of the ADAR1, the constitutive isoform mRNA of ADAR1 (ADAR1b) is 48 fold more expressed and that the same ratio was found in the Human cortex. In SH-SY5Y cells as in Human cerebral cortex total RNA, a reproducible quantity of specific mRNA coding for the 5-HT2cR can be identified. That was not the case for HTB14 cells in which the mRNA coding for the receptor was not expressed in a range allowing constant expression.

Another point was to verify the capacities of these enzymes to respond to classical models of selective induction and to reveal the complex cooperative activity to generate the products of the editing profiles. The validation of these criteria are illustrated on the following two tables.

TABLE 6

Table 6: ADAR1 mRNA and protein expression in IFNα-treated SH-SY5Y cells.

| | RQ mRNA Untreated cells | RQ mRNA IFN-treated cells (1000 IU/ml-48 h) | OD protein (western blot) Untreated cells | OD protein (western-blot) IFN-treated cells (1000 IU/ml-48 h) |
|---|---|---|---|---|
| ADAR1a | 1 | 10.3 | 1 (22.12 OD) | 12.1 (268 OD) |
| ADAR1b | 21.7 | | 116.2 (2570 OD) | 117.1 (2590 OD) |

SH-SY5Y cells were cultured for 48 hours in presence of IFNα at a concentration of 1000 IU/ml. After treatment, total RNA and protein extracts were prepared as described in Materials and Methods. Quantification of mRNA levels of expression was performed by TaqMan quantitative real-time PCR analysis (Q-PCR) on a Applied Biosystems StepOne-Plus™ 96-well apparatus (Applied Biosystems, ref. 4376592). Probes used for Q-PCR were from Applied Biosystems (Gene Expression Assays, Assay-On-Demand): ADAR1 p110 constitutive isoform (Hs 01017596_m1), ADAR1 p150 inducible isoform (Hs 01020780_m1). Human GAPDH (Applied Biosystems, ref. 4326317E) was included in each multiplex Q-PCR as an internal control. RQ were calculated as described by the furnisher. Expression of the ADAR1a gene was taken as a reference and its RQ equal to 1.

TABLE 6-continued

Table 6: ADAR1 mRNA and protein expression in IFNα-treated SH-SY5Y cells.

| | RQ mRNA Untreated cells | RQ mRNA IFN-treated cells (1000 IU/ml-48 h) | OD protein (western blot) Untreated cells | OD protein (western-blot) IFN-treated cells (1000 IU/ml-48 h) |
|---|---|---|---|---|

Protein extracts were resolved by SDS-PAGE on a 12% acrylamide denaturing gel and transferred to a PROTRAN BA 85 nitrocellulose membrane (Whatman, ref. 10 401 197). For ADAR1 proteins detection, nitrocellulose membranes were blotted with a L-15 affinity purified goat polyclonal antibody (Santa Cruz, ref. sc-19077). Bands corresponding to both constitutive (p110) and inducible (p150) ADAR1 isoforms are shown with arrows. Protein standards are also depicted (Precision Plus Protein Standards, Bio-Rad, ref. 161-0363). Bands corresponding to proteins of interest were scanned with the Li—C or Odissey apparatus and further quantified with the MCID software (see FIG. 5). The optical density (OD) obtained for each scan and each experimental condition is shown between brackets (see Table 6). By convention, the OD of ADAR1a isoform in untreated cells was taken as a reference and equal to 1.

This experiment clearly demonstrates that in the culture conditions expressed above the chosen cell line respond to the induction produced by INFα can be observed at the enzymatic protein level with the same specificity and amplitude ratio than those predicted by the mRNA quantification.

The analysis of the distribution of the products of these editing enzymes (index of their activities) was performed by using the SSCP-CE technology previously described in Example 3A and which allows to quantify in one single assay from a sample of total RNA, the total profile of distribution of all the expressed edited and non edited iso forms of the 5-HT2cR mRNA. The table 8 gives an example of editing profiles obtained from 3 limbic cortical structures and SHSY5Y cell line in control conditions.

TABLE 8

Comparison of the editing profiles of 5-HT2cR determined in 3 area of the human brain of control subjects and in the cultured SH-SY5Y cells in control conditions.

| DPFCx Isoforms | Controls Mean (%) | SEM | ACCX Isoforms | Controls Mean (%) | SEM | Entorhinal Cx Isoforms | Controls Mean (%) | SEM | SH-SY5Y cells Isoforms | Controls Mean (%) | SEM |
|---|---|---|---|---|---|---|---|---|---|---|---|
| ABCD (VSV) | 11.67 | 1.01 | ABCD (VSV) | 15.14 | 1.82 | ABCD (VSV) | 11.75 | 1.84 | NE (INI) | 54.0 | 2.9 |
| A (VNI) | 10.14 | 1.83 | AD (VNV) | 9.07 | 1.67 | A (VNI) | 10.41 | 1.11 | A (VNI) | 29.5 | 3.4 |
| ABD (VNV) | 8.51 | 0.66 | NE (INI) | 7.95 | 1.13 | NE (INI) | 9.54 | 1.54 | AC (VSI) | 3.9 | 0.6 |
| NE (INI) | 8.01 | 1.28 | ABD (VNV) | 7.73 | 0.56 | ABD (VNV) | 8.33 | 0.73 | B (MNI) | 2.0 | 0.5 |
| AD (VNV) | 7.01 | 1.31 | A (VNI) | 7.42 | 0.87 | AD (VNV) | 6.71 | 1.07 | AB (VNI) | 1.9 | 0.7 |
| ACE (VGI) | 5.02 | 0.93 | C (ISI) | 5.03 | 0.47 | ACE (VGI) | 5.67 | 0.68 | D (INV) | 1.8 | 1.0 |
| DE (IDV) | 4.57 | 0.45 | ACE (VGI) | 4.77 | 1.12 | AC (VSI) | 5.33 | 0.73 | ABC (VSI) | 1.7 | 0.5 |
| C (ISI) | 4.56 | 0.89 | ABC (VSI) | 4.10 | 0.18 | ACD (VSV) | 3.50 | 0.34 | C (ISI) | 1.2 | 0.4 |
| ABC (VSI) | 4.30 | 0.85 | DE (IDV) | 3.82 | 0.23 | C (ISI) | 3.41 | 0.68 | CE (IGI) | 0.9 | 0.3 |
| ACDE (VGV) | 3.91 | 0.59 | AC (VSI) | 3.81 | 0.72 | DE (IDV) | 3.40 | 0.39 | BC (MSI) | 0.5 | 0.4 |
| AC (VSI) | 3.84 | 1.25 | AB (VNI) | 3.45 | 0.29 | D (INV) | 3.07 | 0.18 | BCD (MSV) | 0.4 | 0.1 |
| ACD (VSV) | 3.31 | 0.18 | ACD (VSV) | 3.26 | 0.52 | BD (MNV) | 3.03 | 0.10 | CD (ISV) | 0.3 | 0.2 |
| AB (VNI) | 3.12 | 0.67 | D (INV) | 3.08 | 0.41 | CD (ISV) | 2.71 | 0.31 | ABD (VNV) | 0.3 | 0.1 |
| D (INV) | 2.70 | 0.31 | ACDE (VGV) | 2.66 | 0.53 | AB (VNI) | 2.36 | 0.95 | ACE (VGI) | 0.3 | 0.0 |
| BD (MNV) | 2.68 | 0.35 | CD (ISV) | 2.47 | 0.42 | ADE (VDV) | 1.96 | 0.75 | ACD (VSV) | 0.2 | 0.0 |
| ABCE (VGI) | 2.43 | 0.57 | BD (MNV) | 2.18 | 0.09 | E (IDI) | 1.79 | 0.16 | AE (VDI) | 0.2 | 0.1 |
| CD (ISV) | 2.15 | 0.15 | ABCDE (VGV) | 1.97 | 0.74 | BC (MSI) | 1.56 | 0.39 | BCE (MGI) | 0.2 | 0.1 |
| ABE (VDI) | 1.82 | 0.22 | ABE (VDI) | 1.86 | 0.17 | ABCDE (VGV) | 1.54 | 0.41 | E (IDI) | 0.1 | 0.1 |
| B (MNI) | 1.44 | 0.36 | ABCDE (VGI) | 1.49 | 0.26 | ABE (VDI) | 1.50 | 0.10 | CDE (IGV) | 0.1 | 0.10 |
| ADE (VDV) | 1.19 | 0.10 | B (MNI) | 1.24 | 0.37 | AE (VDI) | 1.45 | 0.35 | DE (IDV) | 0.1 | 0.1 |
| BCE (MGI) | 0.96 | 0.06 | CE (IGI) | 1.11 | 0.25 | B (MNI) | 1.43 | 0.45 | ABCE (VGI) | 0.1 | 0.0 |
| BCDE (MGV) | 0.86 | 0.09 | ADE (VDV) | 1.03 | 0.11 | ABC (VSI) | 1.39 | 0.28 | ABCDE (VGV) | 0.1 | 0.0 |
| CE (IGI) | 0.81 | 0.09 | BCE (MGI) | 0.99 | 0.09 | ABDE (VDV) | 1.26 | 0.37 | ACDE (VGV) | 0.1 | 0.0 |
| CDE (IGV) | 0.64 | 0.09 | BC (MSI) | 0.97 | 0.15 | CE (IGI) | 1.26 | 0.18 | BE (MDI) | 0.1 | 0.0 |
| ABDE (VDV) | 0.59 | 0.22 | BCDE (MGV) | 0.95 | 0.12 | ABCE (VGI) | 1.08 | 0.32 | ABDE (VDV) | 0.0 | 0.0 |
| BCD (MSV) | 0.42 | 0.10 | ABDE (VDV) | 0.93 | 0.27 | CDE (IGV) | 1.05 | 0.15 | ADE (VDV) | 0.0 | 0.0 |
| BE (MDI) | 0.31 | 0.26 | CDE (IGV) | 0.70 | 0.17 | BCDE (MGV) | 0.92 | 0.11 | ABE (VDI) | 0.0 | 0.0 |
| BC (MSI) | 0.29 | 0.14 | BCD (MSV) | 0.44 | 0.13 | BCD (MSV) | 0.74 | 0.14 | BDE (MDV) | 0.0 | 0.0 |
| AE (VDI) | 0.16 | 0.08 | AE (VDI) | 0.37 | 0.24 | ACDE (VGV) | 0.69 | 0.24 | BCDE (MGV) | 0.0 | 0.0 |
| BDE (MDV) | 0.0 | 0.0 | BDE (MDV) | 0.00 | 0.00 | BCE (MGI) | 0.67 | 0.05 | ABCD (VSV) | 0.0 | 0.0 |
| BE (MDI) | 0.00 | 0.00 | BE (MDI) | 0.00 | 0.00 | BDE (MDV) | 0.37 | 0.29 | AD (VNV) | 0.0 | 0.0 |
| E (IDI) | 0.00 | 0.00 | E (IDI) | 0.00 | 0.00 | BE (MDI) | 0.11 | 0.07 | BD (MNV) | 0.0 | 0.0 |
| | Mean | Number | | Mean | Number | | Mean | Number | | Mean | Number |
| Total Sum | 100.0 | 32.00 | Total Sum | 100.0 | 32.00 | Total Sum | 100.0 | 32.00 | Total Sum | 100.0 | 32.00 |
| Sum <1% | 4.1 | 11 | Sum <1% | 2.4 | 7 | Sum <1% | 3.5 | 6 | Sum <1% | 4.1 | 16 |
| Sum >=1% | 93.3 | 21 | Sum >=1% | 97.6 | 25 | Sum >=1% | 96.5 | 26 | Sum >=1% | 95.9 | 8 |

We can note that a reproducible editing profile can be observed from individual dishes of culture (n = 8). We note than the number of edited isoforms is smaller in the cell line but the mean proportion of isoforms in a range ≥ 1% remains similar indicating a similar efficiency of the analytical process use for the quantification. The shadowed cells indicated the NE isoform proportions and the group of isoforms under a limit of 1%. The results are expressed as the mean % of the total specific mRNA ± SEM (n = 6 control human subjects and 8 cultured dishes in control conditions).

The capacity to rapidly measure these distributions is a prerequisite to correctly investigate the modifications of the activities of editing enzymes which could be produced by pathological states or application of molecules.

Example 6

The Interferon Model: its Interest to Orientate a Specific Strategy to Compare Tested Molecules As previously indicated the interferon α treatment, mainly to treat Hepatitis C, can trigger serious alteration of mood in a large proportion of patients (30 to 50%). It was thus interesting to analyse the effect of INF α upon our selected cell line since (see table 7) this molecule is known to be a strong inducer of ADAR1a inducible isoform of ADAR1.

In a first step the effect of a range of concentrations was evaluated by measuring the degree of expression of this enzyme by QPCR of its specific mRNA. An additional set of experiments was performed to analyse the effect of the product on the editing profile which was considered as a powerful index of editing enzymes activities. The results are summarized on the FIG. 1 and table 4 (see also table 7).

These results have clearly indicated that the induction of ADAR1a was selective and led to a significant alteration of the editing profile mainly concentrated to the AB, ABC and C isoforms. In control conditions these isoforms represented 7.5% of the total specific 5-HT2cR (see table 7). When 1000 IU/ml were applied to the medium for 48 hours, this proportion was found to be 26%. It was thus clear that the induction of ADAR1a affected mainly the production of these isoforms.

In order to statistically analyse these alteration of the profiles and in order to refer to the fact that the comparison was in fact limited to an alteration of a normalized distribution we first classified the observed variations of the mean proportion of the expressed iso forms in function of their algebraic mean delta. This classification was defined as the "signature" of the global modification observed. The variations of the two parts of this signature were then tested by variance analysis. Then the analysis was completed by a component analysis considering groups of iso forms for which a significant alteration of proportions could be detected.

As an example of this process we have decided to use as a reference, a group of significant components deduced from the analysis of the comparison of the signatures obtained from editing profiles of control subjects and depressed suicide patients.

The result of such an analysis is presented on FIG. 3.

Note that, from this analysis, 4 components significantly and positively varied in the 3 human brain structures and 9 components shared a positive significant variation in the 2 prefrontal cortices. The last column of the table illustrates the result of the same analysis performed in SH-SY5Y cultured cells (human origin) after application during 48 hours of human INF alpha at the concentration of 1000 IU/ml. It is interesting to remark the similarity of the signature when compared to components found altered in the 3 cortical structures in depressed-suicide patients. It was thus possible to reasonably propose the use of the same criteria after editing profiling of reference molecules to see if some of them have the capacity to induce similar alteration of the 5-HT2c editing mRNA as observed after INFα application.

Example 7

Use of the In Vitro Platform to the Detection of Reference Molecules Inducing Similar Alteration of the Editing Profile to that Observed after INFα Treatment We decided to use this kind of component analysis to different classes of typical molecules having or not been subjected to FDA alerts concerning mood alteration and suicide risk. An in vitro screening of the editing profile was performed after application of each of them on cultured SH-SY5Y cells for 48 hours at a concentration of 10 µM. The analysis of the editing profiles of 5-HT2c mRNA was performed and analysed with the same set of components defined above (see FIG. 3).

An example of such a classification is given on FIG. 4 and allowed to identify several molecules, belonging to different therapeutic classes, with an activity of 5-HT2cR mRNA editing similarly altered, and potentially presenting, by the fact, a potential risk to induce similar secondary psychiatric effects. Note that Rimonabant and Taranabant belong to this family together with some anti-depressant, anti-psychotic and anti-convulsant molecules.

This kind of analysis of the editing profiles gives the most sensitive criteria allowing to class by "in vitro" screening, molecules sharing common alterations of m RNA editing of a given target. The choice of the components is not limited and can be oriented by several criteria. When this target, here the 5-HT2cR, is directly implicated in the control of mood, circadian rhythms, pain, eating behavior etc., this evaluation can be considered as a valid tool for testing predictive risks of eventual adverse secondary effects for new molecules under pre-clinical investigations.

The invention claimed is:

1. An in vitro method comprising the following steps of:
a) obtaining a biological sample containing mammal cells wherein said mammal cells are cell lines of human origin which exhibit a regular and constitutive expression of the editing enzymes ADAR1a, ADAR1b and ADAR2 and of the serotonin 2C receptor (5HTR2C);
b) contacting said mammals cells with the compound to be tested;
c) determining in the cellular RNA extract of said biological sample:
the editing profile giving the mean proportion of each identified isoform of the 5-HT2CR mRNA measured in the cellular RNA extract, and
the quantitative expression of said editing enzymes ADAR1a, ADAR1b and ADAR2;
d) comparing the results obtained in step c) between said treated cells with the compound to be tested and non treated control cells, and
e) determining the potential toxicity or side-effects of a test compound after its administration in a patient,
wherein in step a), said mammal cells are from the human neuroblastoma SH-SY5Y cell line.

2. An in vitro method comprising the following steps of:
a) obtaining a biological sample containing mammal cells origin which exhibit a regular and constitutive expression of the editing enzymes ADAR1a, ADAR1b and ADAR2 and the 5-HT2C receptor;
b) contacting said mammals cells with the compound to be tested;
c) determining in the cellular RNA extract:
the editing profile giving the mean proportion of each identified isoform of the 5-HT2CR mRNA measured in the cellular RNA extract, and
the quantitative expression of said editing enzymes ADAR1a, ADAR1b and ADAR2;
d) comparing the results obtained in step c) between said treated cells with the compound to be tested and non treated control cells, and
e) selecting a therapeutic compound useful for the treatment of pathology related to an alternation of the mechanism of the MRNA editing of ADAR dependent A to I mRNA edition of the 5HTR2C,
wherein in step a), said mammal cells are from the human neuroblastoma SH-SY5Y cell line.

3. The method according to claim 1, wherein in step c), the editing profile of each identified isoform of the 5-HT2CR mRNA and the quantitative expression of said editing enzymes ADAR1a, ADAR1b and ADAR2 are determined in the same cellular extract.

4. The method according to claim 3, wherein in step c), when the editing profile of each identified isoform of the 5-HT2CR mRNA and the quantitative mRNA expression of said editing enzymes ADAR1a, ADAR1b and ADAR2 are determined in the same cellular extract, they are determined in the same total RNA cell extract.

5. The method according to claim 1, wherein in step c), the analysis of the results of the determination of the editing profile comprises the determination of the activity indexes of these editing enzymes ADAR1a, ADAR1b and ADAR2.

6. The method according to claim 1, wherein in step c), the quantitative expression of said editing enzymes ADAR1a, ADAR1b and ADAR2 is determined by the measure of the mRNA expression of said editing enzymes or by the measure of said editing enzymes protein expressed in the cellular extract.

7. The method according to claim 1, wherein in step a), said mammal cells are cells lines capable of expressing at least one 5HT2CR isoform exhibiting at least the editing site A edited, one 5HT2CR isoform exhibiting at least the editing site B edited, one 5HT2CR isoform exhibiting at least the editing site C edited, one 5HT2CR isoform exhibiting at least the editing site D edited and one 5HT2CR isoform exhibiting at least the editing site E edited, when said mammal cell is treated by a drug capable to alter the edition of the 5HT2CR.

8. The method according to claim 1, wherein in step a), said mammal cells are from a neuroblastoma cell line.

9. The method according to claim 1, wherein potential toxicity or side-effects of said test compound after its administration in a patient is selected from the group consisting of mental disorders, schizophrenia, depression, depressed suicide or abnormal feeding behaviour.

10. The method according to claim 1, wherein in step b) said mammals cells are cultivated in presence of the compound to be tested in a medium suitable for the culture of said mammal cells.

11. The method according to claim 1 wherein in step b) said mammals cells are cultivated in presence of the compound to be tested for at least 1 hour, before the step c) of determining in the same cellular extract the editing profile of each identified isoform of the 5-HT2CR mRNA and/or the quantitative expression of said editing enzymes ADAR1a, ADAR1b and ADAR2.

12. The method according to claim 1, wherein in step c), the editing profile giving the mean proportion of each identified isoform of the 5-HT2CR mRNA measured in the cellular RNA extract is measured by a CE-SSCP method comprising two rounds of PCR, and wherein the first round of PCR is carried out by the following sets of primers:

for human cell lines:

```
                                           (SEQ ID NO: 1)
Forward: 5'-TGTCCCTAGCCATTGCTGATATGC-3', (SEQ ID NO: 2)
Reverse: 5'-GCAATCTTCATGATGGCCTTAGTC-3';
``` and wherein the second round of PCR is carried out by the following set of primers:
for human cell lines:

```
                                           (SEQ ID NO: 3)
Forward: 5'-ATGTGCTATTTTCAACAGCGTCCATC-3', (SEQ ID NO: 4)
Reverse: 5'-GCAATCTTCATGATGGCCTTA-3'.
```

13. The method according to claim 1, wherein in step c), the pair of primers specific for the ADAR mRNA PCR amplification are selected from the group consisting of:
for human ADAR1-150 isoform mRNA amplification:

```
                                           (SEQ ID NO: 7)
Forward: 5'-GCCTCGCGGGCGCAATGAATCC-3'

(SEQ ID NO: 8)
Reverse: 5'-CTTGCCCTTCTTTGCCAGGGAG-3'
``` for human ADAR1-110 isoform mRNA amplification:

```
                                           (SEQ ID NO: 9)
Forward: 5'-CGAGCCATCATGGAGATGCCCTCC-3'

(SEQ ID NO: 10)
Reverse: 5'-CATAGCTGCATCCTGCTTGGCCAC-3'
``` for human ADAR2 mRNA amplification:

```
                                           (SEQ ID NO: 11)
Forward: 5'-GCTGCGCAGTCTGCCCTGGCCGC-3'

(SEQ ID NO: 12)
Reverse: 5'-GTCATGACGACTCCAGCCAGCAC-3'.
```

14. An in vitro method of predicting the potential toxicity of test compounds or for the selection of therapeutical compounds useful for the treatment of pathology related to an alteration of the mechanism of the mRNA editing of ADAR dependent A to I mRNA editing of the serotonin 2C receptor (5HTR2C), which comprises:
(a) screening compounds on a mammal cell line which exhibit a regular and constitutive expression of the 5HT2CR, ADAR1 and ADR2 enzymes for their ability to alter the 5HT2CR edition, these compounds being known to have or not toxicity or side-effects, wherein said mammal cell is from the human neuroblastoma SH-SY5Y cell line;
(b) based on said screening, selecting a panel of reference members, said panel comprising members which differ with respect to their ability to alter the 5HT2CR edition;
(c) screening a test compound of unknown activity relative to said 5HT2CR edition to determine its effect on the alteration on the 5HT2CR edition, thereby obtaining the edition profile of the 5HT2CR;
(d) comparing the edition profile of the 5HT2CR;
(e) predicting the potential toxicity of test compounds or selecting the test compound as potential therapeutical compounds useful for the treatment of pathology related to an alteration of the mechanism of the mRNA editing 5HTR2C, based on the assumption that the alteration of the 5HTR2C edition resulting from the test compound will be similar to that of reference compound,
wherein screening steps on said mammal cell line for their ability to alter the 5HT2CR profile edition corresponds to step c) of claim 1 and wherein the editing profile of each identified isoform of the 5-HT2CR mRNA and the quantitative expression of said editing enzymes ADAR1a, ADAR1b and ADAR2 are determined.

15. The method according to claim 1, wherein the compound to be tested is further administered in vivo to an animal model suitable to test the same compound and wherein the potential toxicity or side-effects of the test compound after its administration in the animal model can be evaluated by determining the alteration of the mRNA editing of the 5HTR2C and/or the ADAR isoforms expressed in total blood and/or skin sample, or in brain.

16. A kit for the determination of the potential toxicity or side-effects of a test compound after its administration in a patient or for the selection of therapeutical compounds useful for the treatment of pathology related to an alteration of the mechanism of the mRNA editing of ADAR dependent A to I mRNA editing of the 5HTR2C, said kit comprising:
  a) mammal cells from a cell line wherein said cells express the editing enzymes ADAR1a, ADAR1 b and ADAR2 and the serotonin 2C receptor (5HTR2C), wherein said mammal cells are from the human neuroblastoma SH-SY5Y cell line; and
  b) two set of primers for measuring by a quantitative (Q) PCR involving a nested type PCR comprising two rounds of PCR each isoform of the 5-HT2CR mRNA which can be present in a RNA extract of said mammal cells; and
  c) a set of primers for measuring by a quantitative Q-PCR the quantitative expression of the editing enzymes ADAR1a, ADAR1 b and ADAR2.

17. The kit according to claim 16, further comprising a panel of reference members differing with respect to their ability to alter the 5HT2CR edition or/and the edition profile of the 5HT2CR and the ADARs expression for said panel of reference members.

18. The method according to claim 7, wherein in step a), said mammal cells are cells lines capable of expressing all the 5HT2CR edited isoforms, when said mammal cell is treated by a drug capable to alter the edition of the 5HT2CR.

19. The method according to claim 9, wherein the treated pathology related to the alteration of the mRNA editing the 5HTR2C according to claim 2 is selected from the group consisting of mental disorders, schizophrenia, depression, depressed suicide or abnormal feeding behaviour.

20. The method according to claim 11, wherein in step b) said mammals cells are cultivated in presence of the compound to be tested for at least 5 hours.

21. The method according to claim 11, wherein in step b) said mammals cells are cultivated in presence of the compound to be tested for at least 10 hours.

22. The method according to claim 11, wherein in step b) said mammals cells are cultivated in presence of the compound to be tested for at least 16 hours.

23. The method according to claim 11, wherein in step b) said mammals cells are cultivated in presence of the compound to be tested for at least 24 hours.

24. An in vitro method according to claim 14, wherein in step a) said mammal cell line is a neuroblastoma cell line.

25. An in vitro method according to claim 14, wherein in step b) said panel comprises members which differ with respect to their toxicity or side-effects.

26. An in vitro method according to claim 14, wherein step c) comprises the determination of the ADARs expression for said test compound.

27. An in vitro method according to claim 14, wherein step d) comprises the determination of the ADARs expression for said test compound and for said panel of references.

28. An in vitro method according to claim 14, comprising the determination of the ADARs expression.

29. A method according to claim 15, wherein the compound to be tested is administered in vivo to a mouse or a rat.

* * * * *

SEQUENCE LISTING

```
<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Description of the artificial sequence :
      sequence derived from the cDNA coding for 5-HT2C receptor

<400> SEQUENCE: 1
tgtccctagc cattgctgat atgc                                            24

<210> SEQ ID NO 2
<211> LENGTH: 24
```

```
<212> TYPE: DNA
<213> ORGANISM: Artificial Sequence
<220> FEATURE:
<223> OTHER INFORMATION: Description of the artificial sequence :
      sequence derived from the cDNA coding for 5-HT2C receptor

<400> SEQUENCE: 2
gcaatcttca tgatggcctt agtc                                              24

<210> SEQ ID NO 3
<211> LENGTH: 26
<212> TYPE: DNA
<213> ORGANISM: Artificial Sequence
<220> FEATURE:
<223> OTHER INFORMATION: Description of the artificial sequence :
      sequence derived from the cDNA coding for 5-HT2C receptor

<400> SEQUENCE: 3
atgtgctatt ttcaacagcg tccatc                                            26

<210> SEQ ID NO 4
<211> LENGTH: 21
<212> TYPE: DNA
<213> ORGANISM: Artificial Sequence
<220> FEATURE:
<223> OTHER INFORMATION: Description of the artificial sequence :
      sequence derived from the cDNA coding for 5-HT2C receptor

<400> SEQUENCE: 4
gcaatcttca tgatggcctt a                                                 21

<210> SEQ ID NO 5
<211> LENGTH: 18
<212> TYPE: DNA
<213> ORGANISM: Artificial Sequence
<220> FEATURE:
<223> OTHER INFORMATION: Description of the artificial sequence :
      sequence derived from the cDNA coding for 5-HT2C receptor

<400> SEQUENCE: 5
tttgtgcccc gtctggat                                                     18

<210> SEQ ID NO 6
<211> LENGTH: 18
<212> TYPE: DNA
<213> ORGANISM: Artificial Sequence
<220> FEATURE:
<223> OTHER INFORMATION: Description of the artificial sequence :
      sequence derived from the cDNA coding for 5-HT2C receptor

<400> SEQUENCE: 6
gccttagtcc gcgaattg                                                     18

<210> SEQ ID NO 7
<211> LENGTH: 22
<212> TYPE: DNA
<213> ORGANISM: Artificial Sequence
<220> FEATURE:
<223> OTHER INFORMATION: Description of the artificial sequence :
      sequence derived from the cDNA coding for human ADAR1 150 isoform

<400> SEQUENCE: 7
gcctcgcggg cgcaatgaat cc                                                22

<210> SEQ ID NO 8
<211> LENGTH: 22
<212> TYPE: DNA
```

<213> ORGANISM: Artificial Sequence
<220> FEATURE:
<223> OTHER INFORMATION: Description of the artificial sequence :
      sequence derived from the cDNA coding for human ADAR1 150 isoform

<400> SEQUENCE: 8
cttgcccttc tttgccaggg ag                                                 22

<210> SEQ ID NO 9
<211> LENGTH: 24
<212> TYPE: DNA
<213> ORGANISM: Artificial Sequence
<220> FEATURE:
<223> OTHER INFORMATION: Description of the artificial sequence :
      sequence derived from the cDNA coding for human ADAR1 110 isoform

<400> SEQUENCE: 9
cgagccatca tggagatgcc ctcc                                               24

<210> SEQ ID NO 10
<211> LENGTH: 24
<212> TYPE: DNA
<213> ORGANISM: Artificial Sequence
<220> FEATURE:
<223> OTHER INFORMATION: Description of the artificial sequence :
      sequence derived from the cDNA coding for human ADAR1 110 isoform

<400> SEQUENCE: 10
catagctgca tcctgcttgg ccac                                               24

<210> SEQ ID NO 11
<211> LENGTH: 23
<212> TYPE: DNA
<213> ORGANISM: Artificial Sequence
<220> FEATURE:
<223> OTHER INFORMATION: Description of the artificial sequence :
      sequence derived from the cDNA coding for human ADAR2

<400> SEQUENCE: 11
gctgcgcagt ctgccctggc cgc                                                23

<210> SEQ ID NO 12
<211> LENGTH: 23
<212> TYPE: DNA
<213> ORGANISM: Artificial Sequence
<220> FEATURE:
<223> OTHER INFORMATION: Description of the artificial sequence :
      sequence derived from the cDNA coding for human ADAR2

<400> SEQUENCE: 12
gtcatgacga ctccagccag cac                                                23

<210> SEQ ID NO 13
<211> LENGTH: 22
<212> TYPE: DNA
<213> ORGANISM: Artificial Sequence
<220> FEATURE:
<223> OTHER INFORMATION: Description of the artificial sequence :
      sequence derived from the cDNA coding for murine ADAR1 150 isoform

<400> SEQUENCE: 13
gtctcaaggg ttcaggggac cc                                                 22

<210> SEQ ID NO 14
<211> LENGTH: 24
<212> TYPE: DNA
<213> ORGANISM: Artificial Sequence

```
<220> FEATURE:
<223> OTHER INFORMATION: Description of the artificial sequence :
      sequence derived from the cDNA coding for murine ADAR1 150 isoform

<400> SEQUENCE: 14
ctcctctagg gaattcctgg atac                                              24

<210> SEQ ID NO 15
<211> LENGTH: 23
<212> TYPE: DNA
<213> ORGANISM: Artificial Sequence
<220> FEATURE:
<223> OTHER INFORMATION: Description of the artificial sequence :
      sequence derived from the cDNA coding for murine ADAR1 110 isoform

<400> SEQUENCE: 15
tcacgagtgg gcagcgtccg agg                                               23

<210> SEQ ID NO 16
<211> LENGTH: 23
<212> TYPE: DNA
<213> ORGANISM: Artificial Sequence
<220> FEATURE:
<223> OTHER INFORMATION: Description of the artificial sequence :
      sequence derived from the cDNA coding for murine ADAR2

<400> SEQUENCE: 16
gctgcacagt ctgccttggc tac                                               23

<210> SEQ ID NO 17
<211> LENGTH: 24
<212> TYPE: DNA
<213> ORGANISM: Artificial Sequence
<220> FEATURE:
<223> OTHER INFORMATION: Description of the artificial sequence :
      sequence derived from the cDNA coding for murine ADAR2

<400> SEQUENCE: 17
gcataaagaa acctgagcag ggac                                              24
```